United States Patent
Penny et al.

(10) Patent No.: US 10,945,800 B2
(45) Date of Patent: *Mar. 16, 2021

(54) PATIENT-SIDE MECHANIZED SURGICAL SYSTEM

(71) Applicant: GREAT BELIEF INTERNATIONAL LIMITED, Tortola (VG)

(72) Inventors: Matthew R Penny, Holly Springs, NC (US); Nicholas J Bender, Raleigh, NC (US); Mohan Nathan, Raleigh, NC (US); Nicholas J. Jardine, Cary, NC (US); Galen Robertson, Apex, NC (US); Carson Shellenberger, Raleigh, NC (US); Lucas A. Tew, Raleigh, NC (US); Richard M Mueller, Chapel Hill, NC (US); James Cuevas, Santa Barbara, CA (US); Jeff Wilson, Goleta, CA (US); Keith Philip Laby, Oakland, CA (US)

(73) Assignee: GREAT BELIEF INTERNATIONAL LIMITED, Tortola (VG)

( * ) Notice: Subject to any disclaimer, the term of this patent is extended or adjusted under 35 U.S.C. 154(b) by 477 days.

This patent is subject to a terminal disclaimer.

(21) Appl. No.: 15/439,915

(22) Filed: Feb. 22, 2017

(65) Prior Publication Data
US 2017/0165019 A1 Jun. 15, 2017

Related U.S. Application Data

(63) Continuation of application No. 13/939,229, filed on Jul. 11, 2013, now Pat. No. 9,603,672, which is a
(Continued)

(51) Int. Cl.
A61B 34/00 (2016.01)
A61B 34/37 (2016.01)
(Continued)

(52) U.S. Cl.
CPC .............. *A61B 34/71* (2016.02); *A61B 19/22* (2013.01); *A61B 34/30* (2016.02); *A61B 34/37* (2016.02);
(Continued)

(58) Field of Classification Search
CPC ... A61B 34/30; A61B 34/37; A61B 2034/305; A61B 2034/301; A61B 2017/00477;
(Continued)

(56) References Cited

U.S. PATENT DOCUMENTS

2011/0208000 A1* 8/2011 Honda ............... A61B 1/00016
600/118

FOREIGN PATENT DOCUMENTS

JP 2009/0148814 * 6/2009

* cited by examiner

*Primary Examiner* — Katherine M Shi
*Assistant Examiner* — Michael G Mendoza

(57) ABSTRACT

A motorized surgical system includes at least one support positionable within a sterile field in proximity to a patient positioned on a surgical table. An instrument driver is carried by the support and includes a steerable distal end positionable in a body cavity. A user input device is carried by the support and is configured to generate movement signals in response to manual manipulation of a portion of the user input device by a user. One or more steering motors are operably coupled to the instrument driver and are operable to deflect the steerable distal end of the instrument driver in response to the movement signals.

13 Claims, 35 Drawing Sheets

Related U.S. Application Data continuation of application No. 13/759,036, filed on Feb. 4, 2013, now Pat. No. 9,333,040.

(60) Provisional application No. 61/594,362, filed on Feb. 2, 2012, provisional application No. 61/714,737, filed on Oct. 16, 2012.

(51) Int. Cl.
*A61B 17/00* (2006.01)
*A61B 34/30* (2016.01)
*A61B 19/00* (2006.01)
*A61B 17/29* (2006.01)
*A61B 17/34* (2006.01)

(52) U.S. Cl.
CPC ........ *A61B 34/70* (2016.02); *A61B 2017/003* (2013.01); *A61B 2017/00477* (2013.01); *A61B 2017/2906* (2013.01); *A61B 2017/3447* (2013.01); *A61B 2019/2211* (2013.01); *A61B 2019/2223* (2013.01); *A61B 2019/2234* (2013.01); *A61B 2019/2242* (2013.01); *A61B 2034/301* (2016.02); *A61B 2034/305* (2016.02)

(58) Field of Classification Search
CPC ...... A61B 2017/003; A61B 2017/2906; A61B 2017/3447
See application file for complete search history.

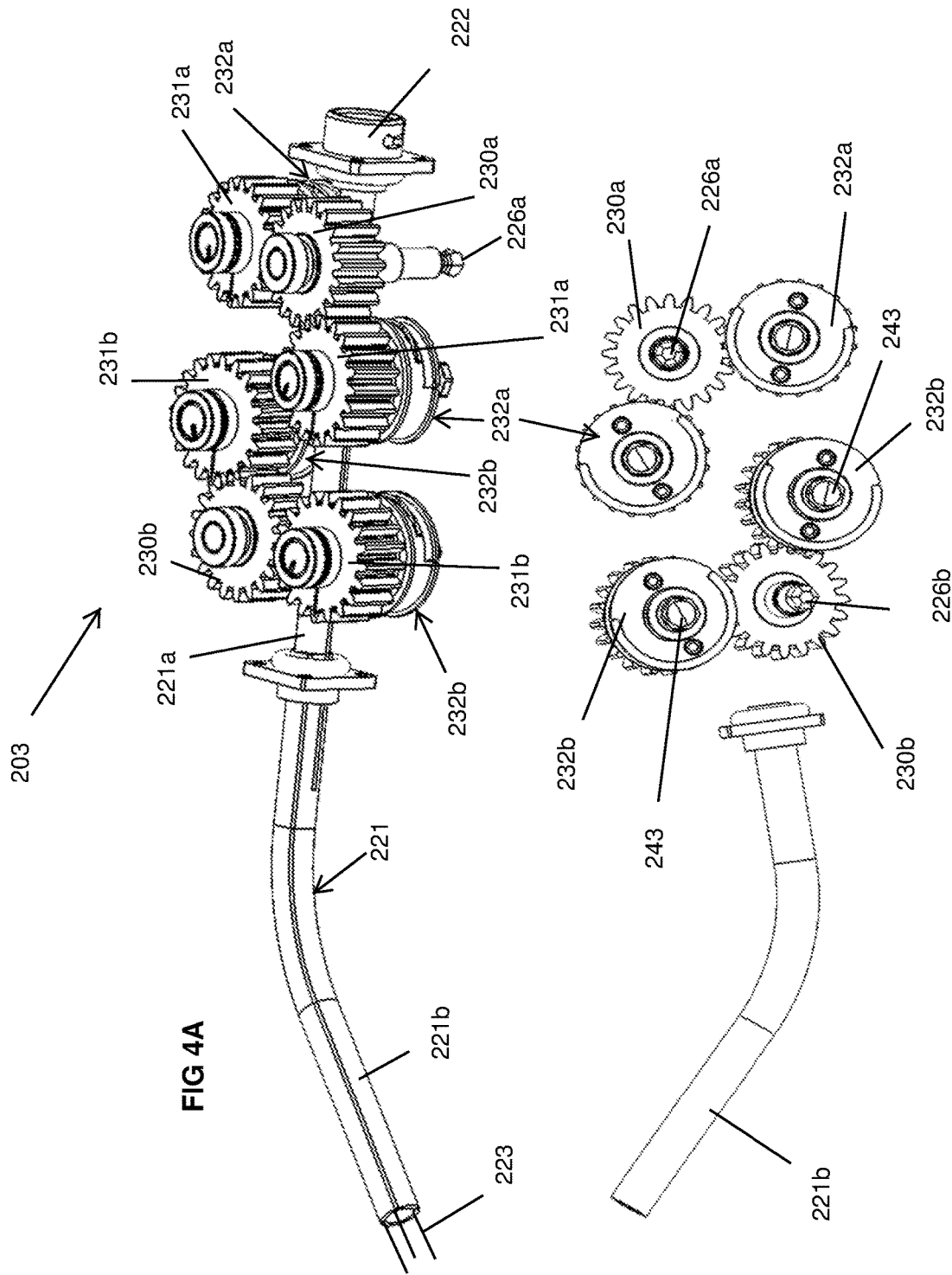

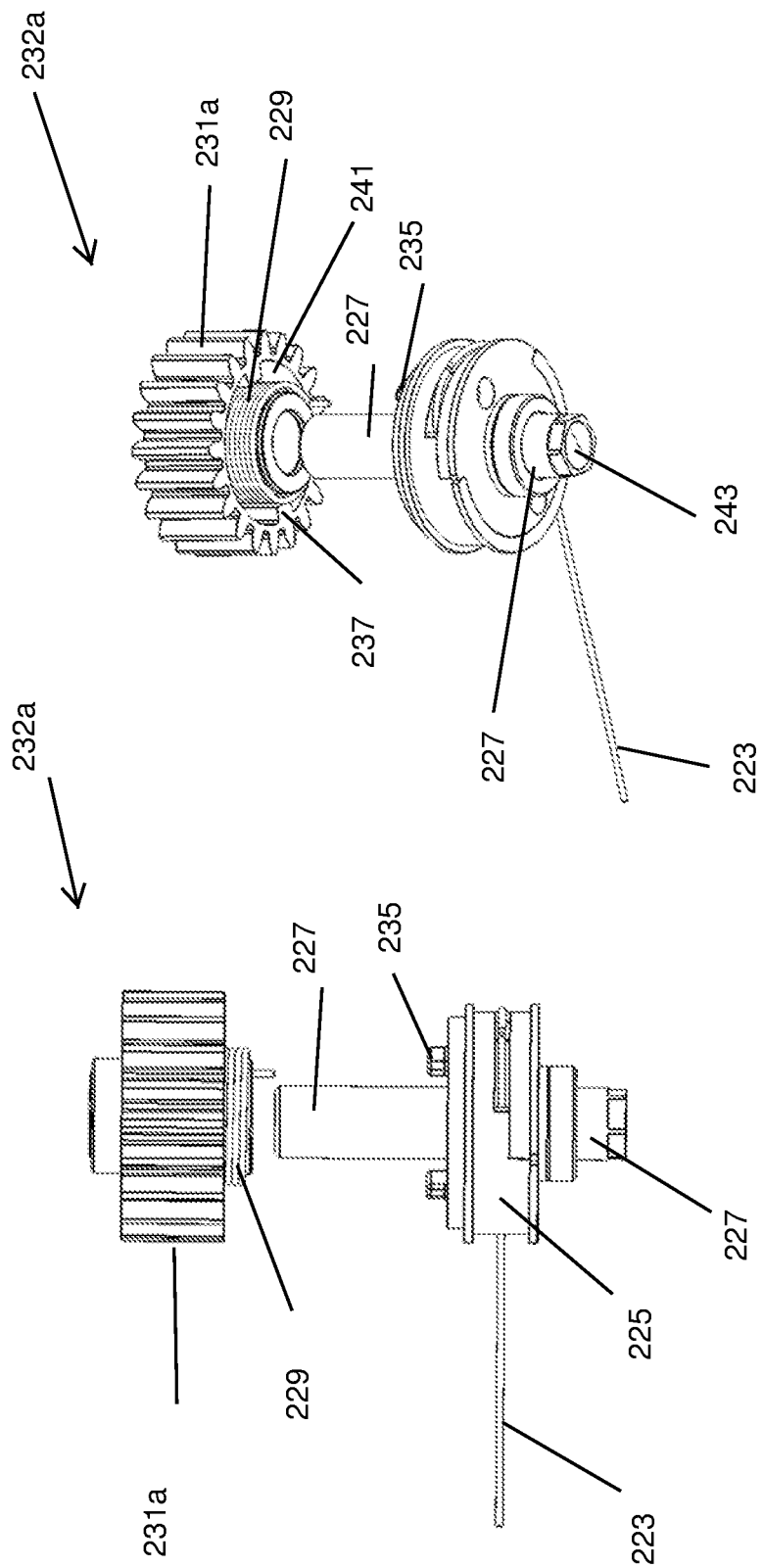

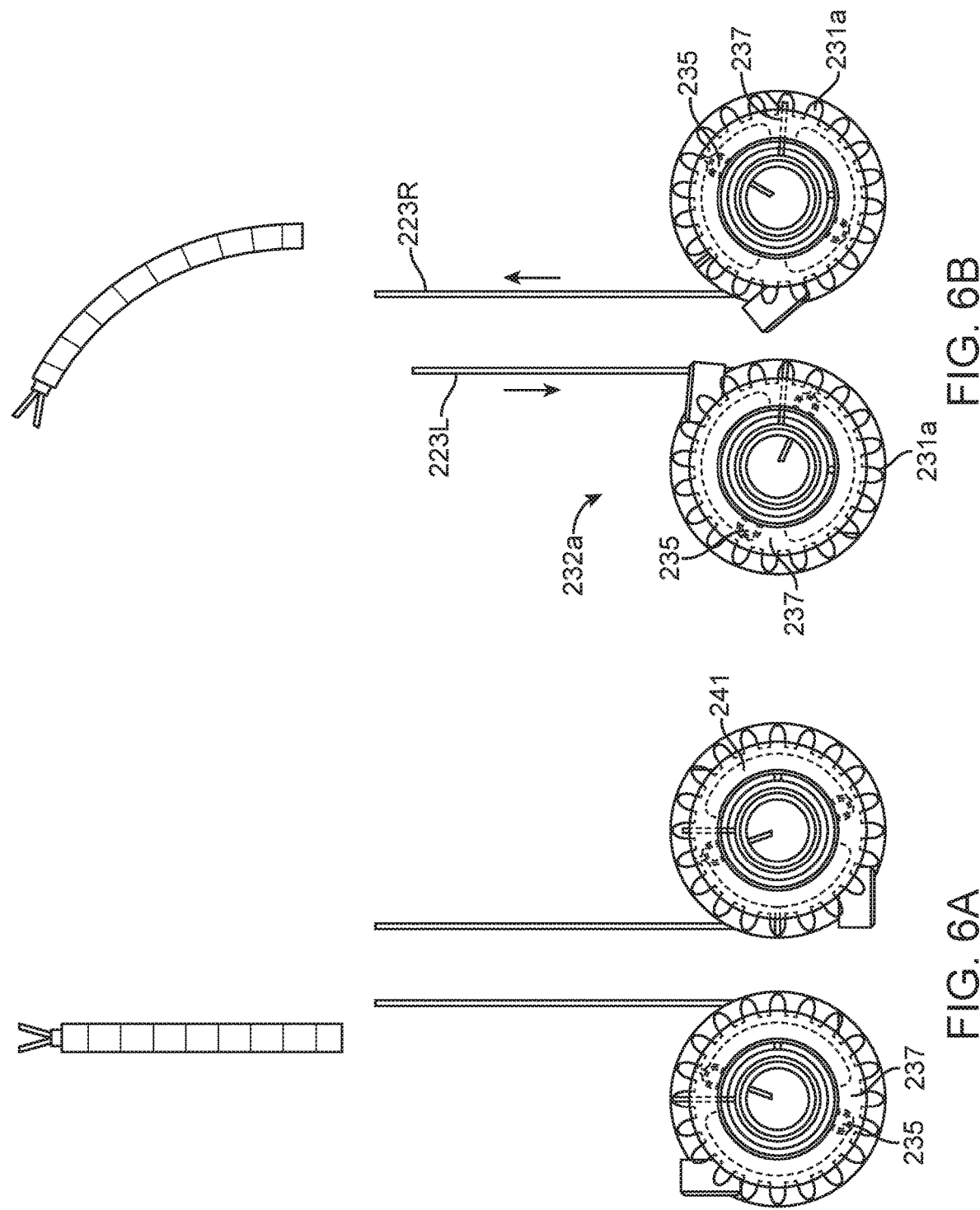

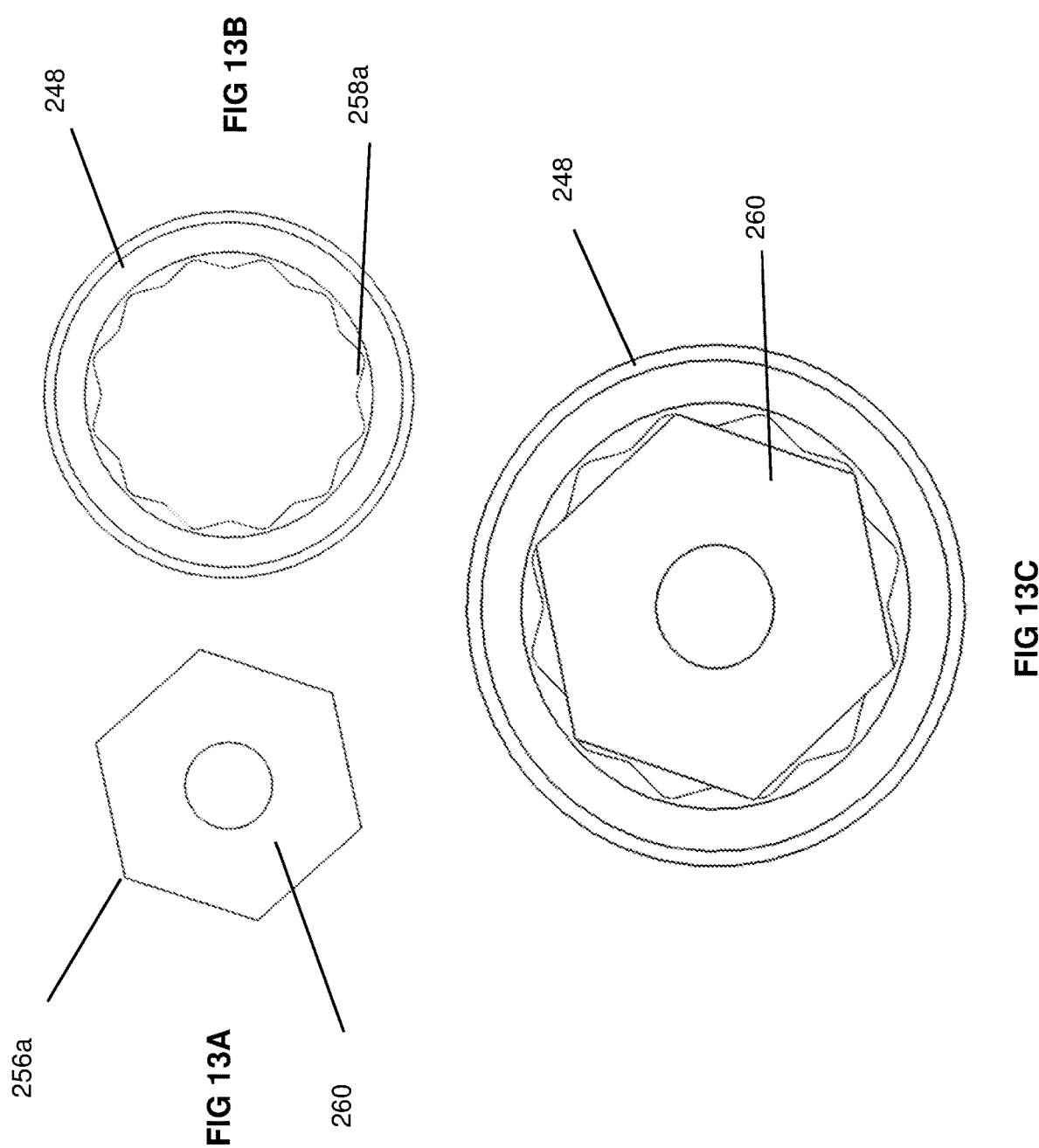

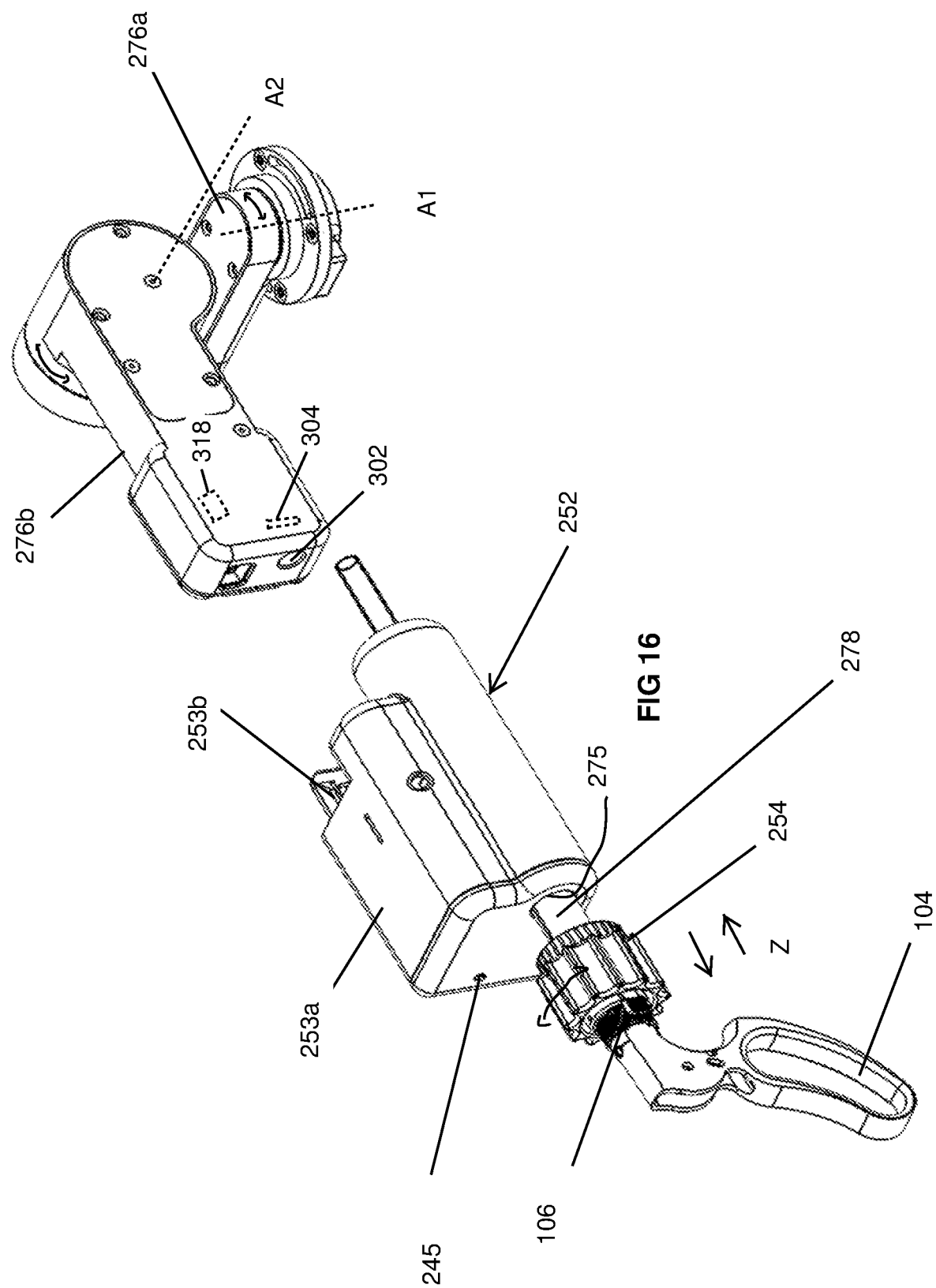

PATIENT-SIDE MECHANIZED SURGICAL SYSTEM

This application is a continuation of U.S. Ser. No. 14/197,157, filed Mar. 5, 2014, which is a continuation of U.S. Ser. No. 13/759,036, now U.S. Pat. No. 9,603,672 filed Feb. 4, 2013, which claims priority to U.S. Provisional Application No. 61/594,362, filed Feb. 2, 2012, and U.S. Provisional Application No. 61/714,737, filed Oct. 16, 2012. Each of the foregoing is incorporated herein by reference.

TECHNICAL FIELD OF THE INVENTION

The present invention relates to the field of access devices and ports through which flexible medical instruments may be introduced into a body cavity and steered or deflected.

BACKGROUND

In conventional laparoscopic procedures, multiple small incisions are formed through the skin, underlying muscle and peritoneal tissue to provide access to the peritoneal cavity for the various medical instruments and scopes needed to complete the procedure. The peritoneal cavity is typically inflated using insufflation gas to expand the cavity, thus improving visualization and working space. In a typical laparoscopic medical procedure, four ports are strategically placed around the abdominal area allowing the surgeon visualization and use of instruments using principles of triangulation to approach the surgical target. While this procedure is very effective and has stood as the gold standard for minimally invasive surgery, it suffers from a number of drawbacks. One such drawback is the need for multiple incisions to place the four ports, which increases the risk of complications such as post-operative herniation and prolonged patient recovery. The four port method also raises concerns of cosmesis, leaving the patient with four abdominal scars.

Further developments have led to systems allowing procedures to be performed using multiple instruments passed through a single incision or port. In some such single port procedures, visualization and triangulation are compromised due to linear instrumentation manipulation, and spatial confinement resulting in what has been known as "sword fighting" between instruments.

Improvements on the prior single port techniques are found in the multi-instrument access devices suitable for use in SPS procedures and other laparoscopic procedures and described in co-pending U.S. application Ser. No. 11/804,063 ('063 application) filed May 17, 2007 and entitled SYSTEM AND METHOD FOR MULTI-INSTRUMENT SURGICAL ACCESS USING A SINGLE ACCESS PORT, U.S. application Ser. No. 12/209,408 filed Sep. 12, 2008 and entitled MULTI-INSTRUMENT ACCESS DEVICES AND SYSTEMS, U.S. application Ser. No. 12/511,043, filed Jul. 28, 2009, entitled MULTI-INSTRUMENT ACCESS DEVICES AND SYSTEMS, and U.S. application Ser. No. 12/649,307, filed Dec. 29, 2009, (US Publication 2011/0230723) entitled ACTIVE INSTRUMENT PORT SYSTEM FOR MINIMALLY-INVASIVE SURGICAL PROCEDURES, each of which is incorporated herein by reference.

U.S. application Ser. No. 12/649,307 (US Publication 2011/0230723) filed Dec. 29, 2009 and entitled ACTIVE INSTRUMENT PORT FOR MINIMALLY-INVASIVE SURGICAL PROCEDURES describes a system for use in performing multi-tool minimally invasive medical procedures using a plurality of instruments passed through a single incision in a body cavity. The disclosed system includes an insertion tube and a pair of instrument delivery tubes (IDTs) extending from the distal end of the insertion tube. Each IDT has steerable distal portion positioned distal to the distal end of the insertion tube. In use, flexible instruments passed through the IDTs are steered by actively deflecting the deflectable distal portions of the IDTs. In particular, proximal actuators (shown as ball-and-socket or gimbal type actuators) for the IDTs are positioned proximally of the insertion tube. Instruments to be deployed from the IDTs into the body cavity are inserted through the proximal actuators into the IDTs. The proximal actuators are moveable in response to manipulation of the handles of instruments extending through the IDTs. Movement of the proximal actuators engages pull elements (e.g. wires, cables etc) that extend from the proximal actuators to the deflectable sections of the IDT's, thus steering the distal portions of the IDTs (and thus the distal ends of the instruments themselves). Additional instruments such as scopes and other instruments may also be passed through the insertion tube (such as through rigid instrument channels) and used simultaneously with the instruments deployed through the IDTs.

Additional examples of proximal actuators and/or IDT shafts that may be used in such access systems are described in U.S. 2011/0184231, entitled DEFLECTABLE INSTRUMENT PORTS, U.S. 2011/0060183, entitled MULTI-INSTRUMENT ACCESS DEVICES AND SYSTEMS, and U.S. 2011/0251599 entitled DEFLECTABLE INSTRUMENT SHAFTS, each of which is incorporated herein by reference.

The present application describes new multi-instrument surgical access systems for use in minimally invasive procedures.

BRIEF DESCRIPTION OF THE DRAWINGS

FIGS. 1B through 18 are various views of components of the first embodiment, in which:

FIG. 1B shows the system supported by an arm and positioned relative to an operating table.

FIG. 3 is a perspective view of a finger driver, including the pulley housing.

FIG. 4A is similar to FIG. 3, but without the pulley housing.

FIG. 4B is a bottom perspective view of the components of the finger driver, without the pulley housing, proximal tube and cables.

FIGS. 5B and 5C are partially exploded views of the pulley of FIG. 5A.

FIGS. 6A and 6B schematically illustrate operation of the pulleys of the finger driver.

FIG. 9 is a perspective view of a roll driver.

FIG. 10 is a perspective view of the roll drive tube and gear assembly of the roll driver.

FIGS. 13A and 13B are end views of an alternative roll drive tube and drive segment, respectively.

FIG. 13C shows rotational engagement of the roll drive tube and drive segment of FIGS. 13A and 13B.

FIG. 14 shows rotational engagement of a second alternative roll drive tube and drive segment.

FIG. 15 is an exploded view of a tubular connector positionable between the housing and roll driver of FIG. 1A.

FIG. 16 is a perspective view of the command interface, showing the instrument box separated from the brackets. The handle of an instrument, but not its distal shaft, is shown.

DETAILED DESCRIPTION

Figure 1A:
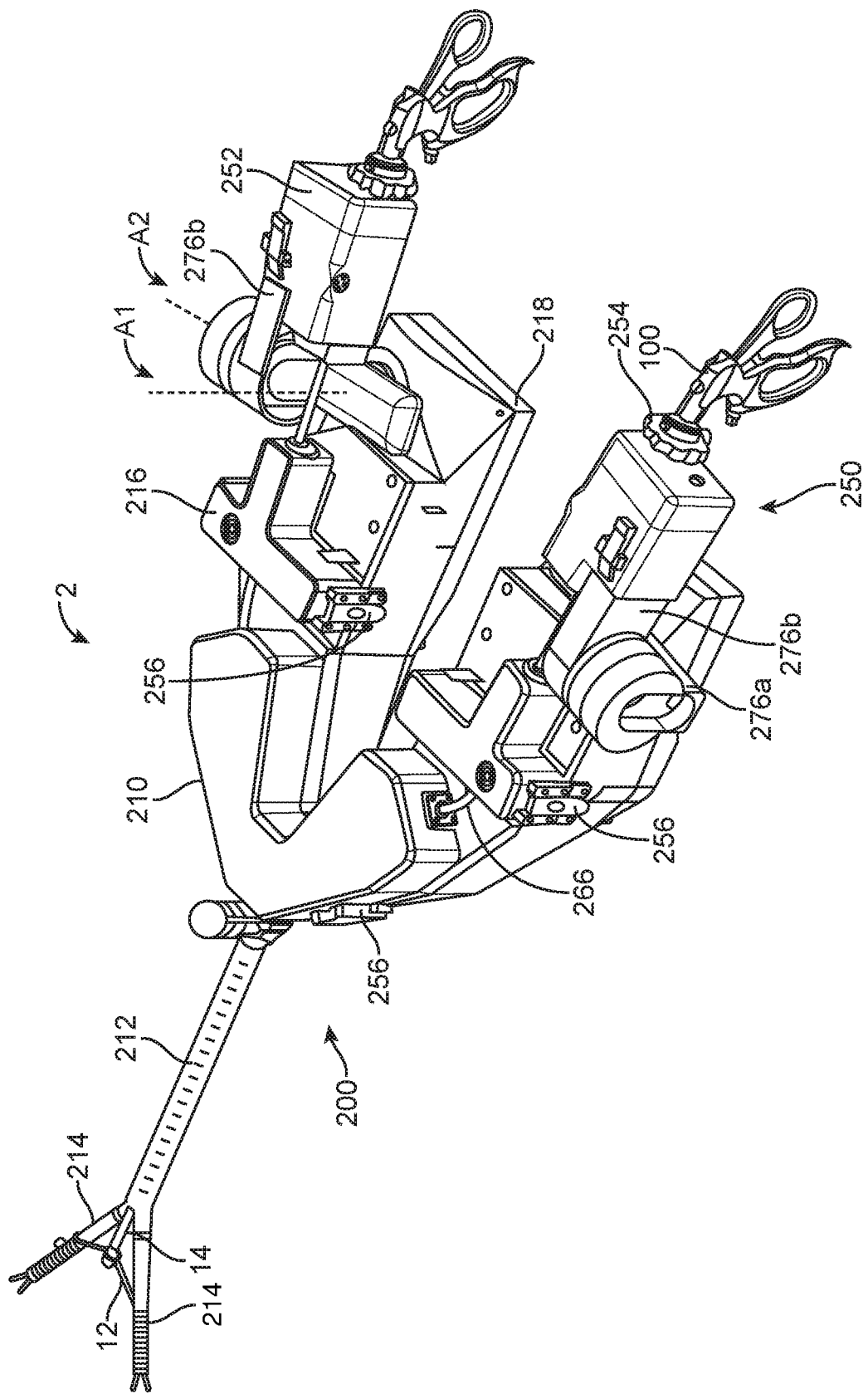
FIG. 1A is a perspective view of a motor-assisted multi-instrument surgical system.

The present application discloses a new motor-assisted multi-instrument surgical system having certain advantages over prior art systems.

Overview

Referring to FIG. 1, a first embodiment of a surgical access system 2 includes a finger drive assembly 200 comprising a housing 210 and an insertion cannula 212 extending distally from the housing 210. Steerable instrument delivery tubes or tubular fingers 214 extend distally from the insertion cannula 212. The tubular fingers 214 have lumen for receiving passively flexible surgical instruments 100. As will be described below, motor-driven finger drivers within the finger drive assembly 200 steer the fingers 214 using cables anchored at the distal ends of the fingers. Associated with each tubular finger 214 is a corresponding motor driven roll driver 216—which acts on a distal portion of the instrument shaft to rotate it axially.

In the first embodiment, the motors used to actuate the finger drivers and the roll drivers, as well as associated controllers and electronics are housed within a base unit 218, and the finger drive assembly 200 and the roll drivers 216 are removably mounted to the base in a manner that delivers motion from the motors to the finger drivers and roll drivers. Spring latches 255 (FIG. 1A) are positioned to engage the finger drive assembly 200 and roll drivers 216 with the base 218 when they are placed on the base in the proper orientation. Alignment features 215 (FIG. 1C) on the upper surface of the base unit 218 mate with or contact corresponding features at the lower surface of the finger drive assembly 200 and roll drivers 216. The alignment features help align the assembled components and to prevent components mounted to the base 218 from sliding relative to the surface of the base during use.

The base unit 218 can be a reusable component isolated from the sterile field using a sterile drape or bag (not shown), whereas the finger drive assembly 200 and roll drivers 216 may be manufactured as single-use components or re-usable components for a number of times prior to disposal. Re-usable components may be designed for autoclaving or other forms of sterilization.

Command interfaces 250 are provided for each of the tubular fingers 214. The command interfaces 250 include instrument boxes 252 that support the instrument handles. The command interfaces 250 are user input devices that generate signals in response to the user's manipulation of the instrument handle (e.g. pan, tilt and roll) and/or other user inputs. In response to signals generated at the command interface 250, the system's motors are controlled to cause the finger driver and roll driver to drive the fingers and instrument in accordance with the user input.

Figure 1B:
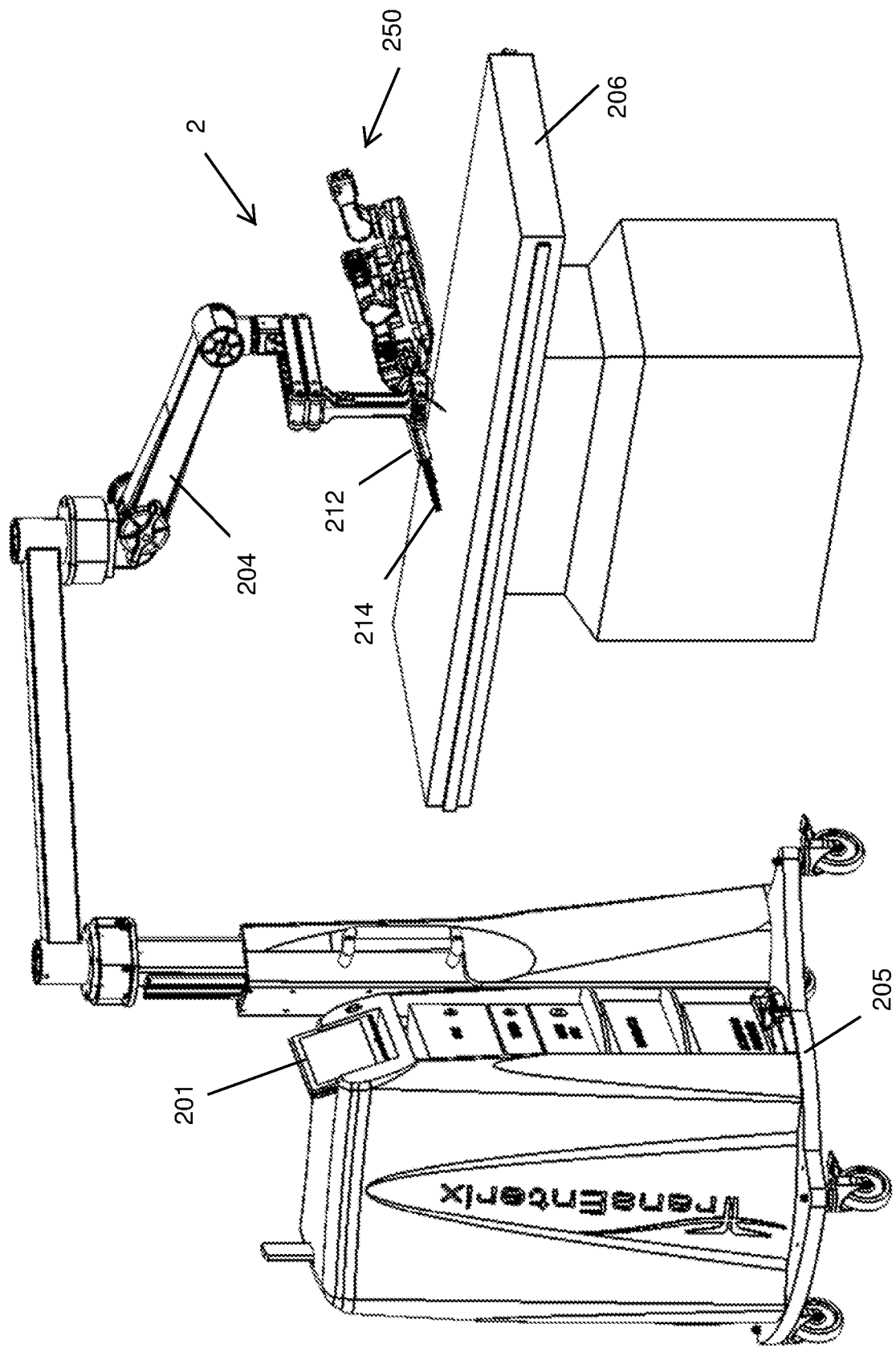

Referring to FIG. 1B, the system 2 is supported by a support arm 204 extending from a patient-side cart 205, the operating table 206, a ceiling mount, or another fixture that positions the arm 204 where it can support the finger and roll drivers, the associated motors, and the command unit near the operating table, allowing the surgeon to stand patient-side with his/her hands on the instruments 100. The arm may be one allowing repositioning of the system 2 in multiple degrees of freedom. While a robotically-controlled arm could be used with the system 2, since control and manipulation of the instruments is achieved using the system 2 rather than maneuvering of the arm 204, the arm may be much simpler in design and smaller in size than those used for conventional robotic surgery. The illustrated arm 204 is manually positionable about multiple joints and lockable in a selected position. Multiple degree of freedom movement allows the user to position the system 2 to place the insertion cannula 212 and the command interfaces 250 in the desired position relative to the patient and the surgeon. The cart 205 can be used to carry other equipment intended for use with the system 2, such as components supporting visualization, insufflations, stapling, electrosurgery, etc. The arm 204 has internal springs which counterbalance the weight of system 2, allowing it to remain stable in space while the arm is unlocked, and reduces the force required to move the system. While many joint combinations are possible the four bar linkages shown in the pictured embodiment allow for the system 2, to pivot about the center of gravity, which reduces the force required to reposition the system.

Figure 18A:
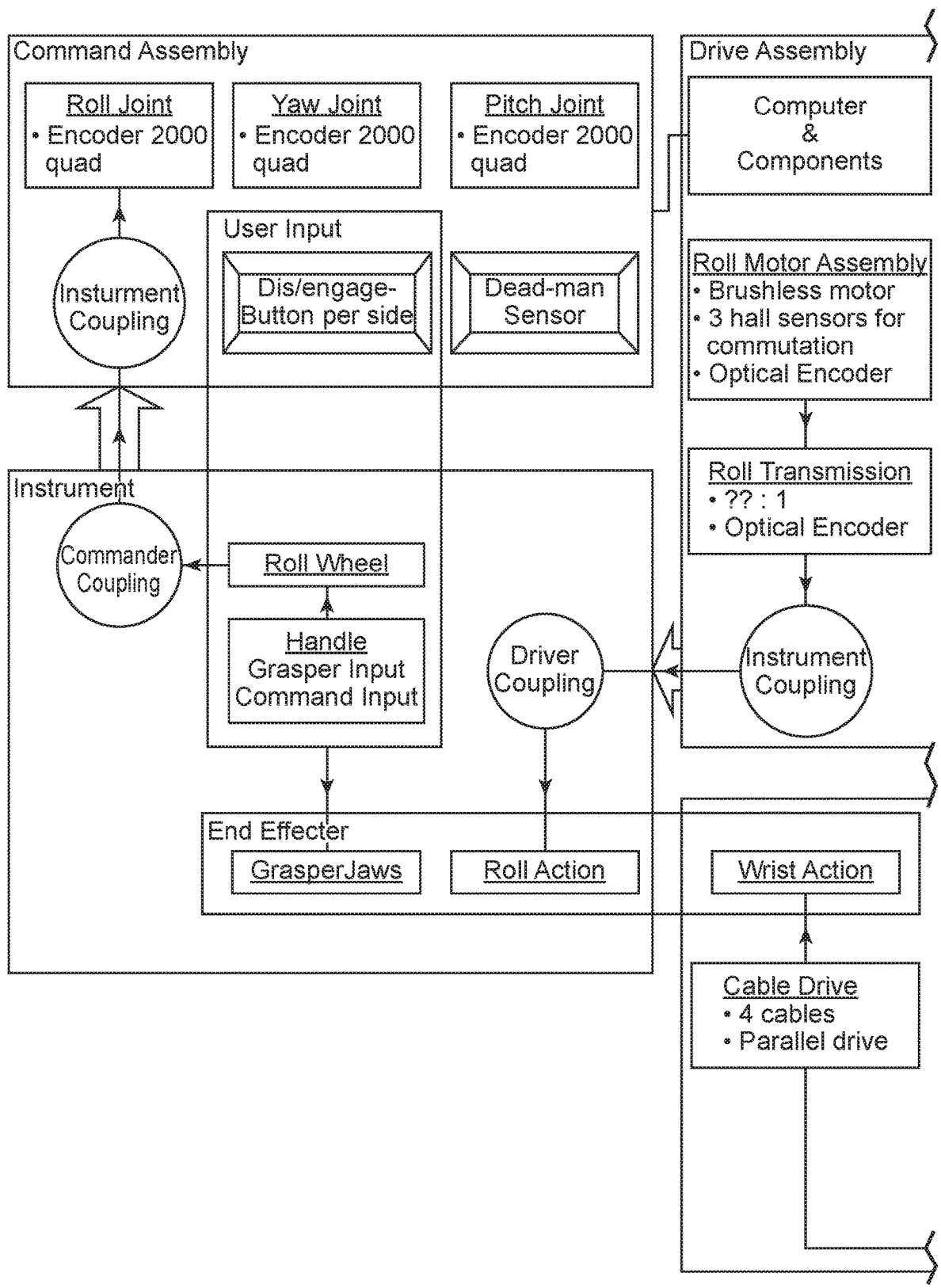
FIG. 18A is a block diagram schematically illustrating components of a variation of the system.
Figure 18A:
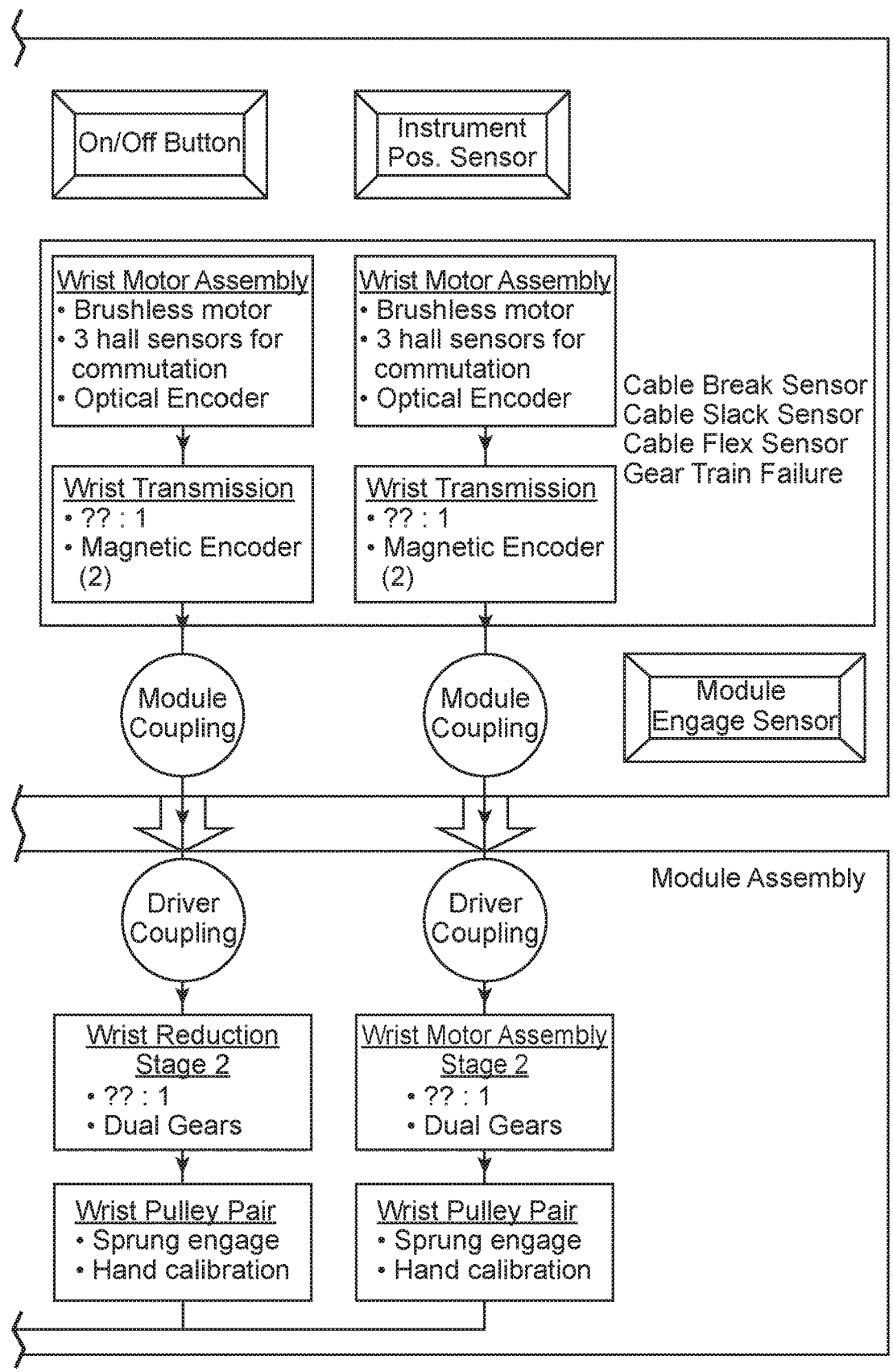

The system's power supply, computer and user controls (e.g. touch screen computer 201), which are discussed with respect to the system schematic at FIG. 18, may be mounted on the cart 205 with their associated cabling routed through the arm 204 to the base unit 218.

A brief overview of the manner in which the system 2 is used will facilitate an understanding of the more specific description of the system given below. During use, the fingers 214 and a portion of the insertion tube 212 are positioned through an incision into a body cavity. The distal end of a surgical instrument 100 is manually, removably, inserted through an instrument box 252 of command interface 250, and the corresponding roll driver 216 and into the corresponding tubular finger 214 via the finger drive assembly 200. The instrument is positioned with its distal tip distal to the distal end of the tubular finger 214, in the patient's body cavity, and such that the handle 104 of the instrument is proximal to the command interface 250.

Figure 11A:
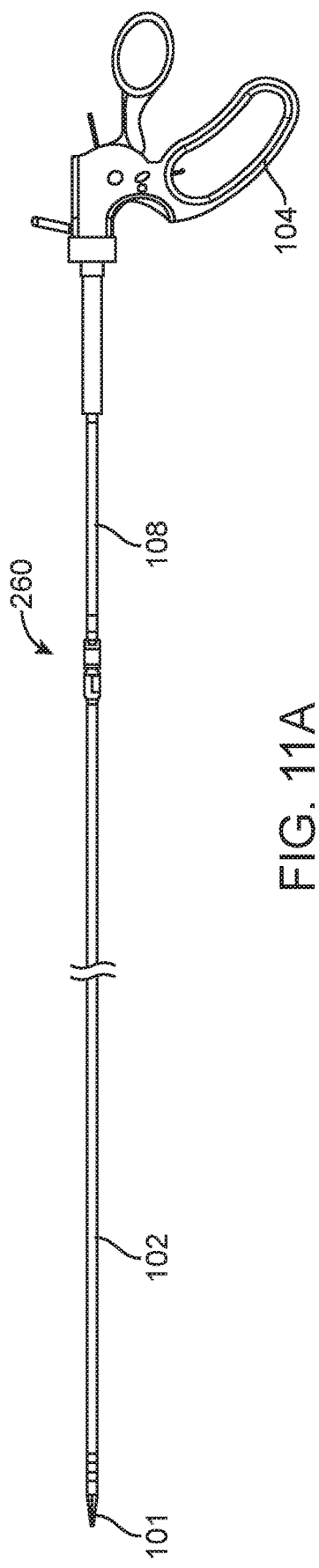
FIG. 11A is a side elevation view of an instrument that may be used with the system.
Figure 11B:
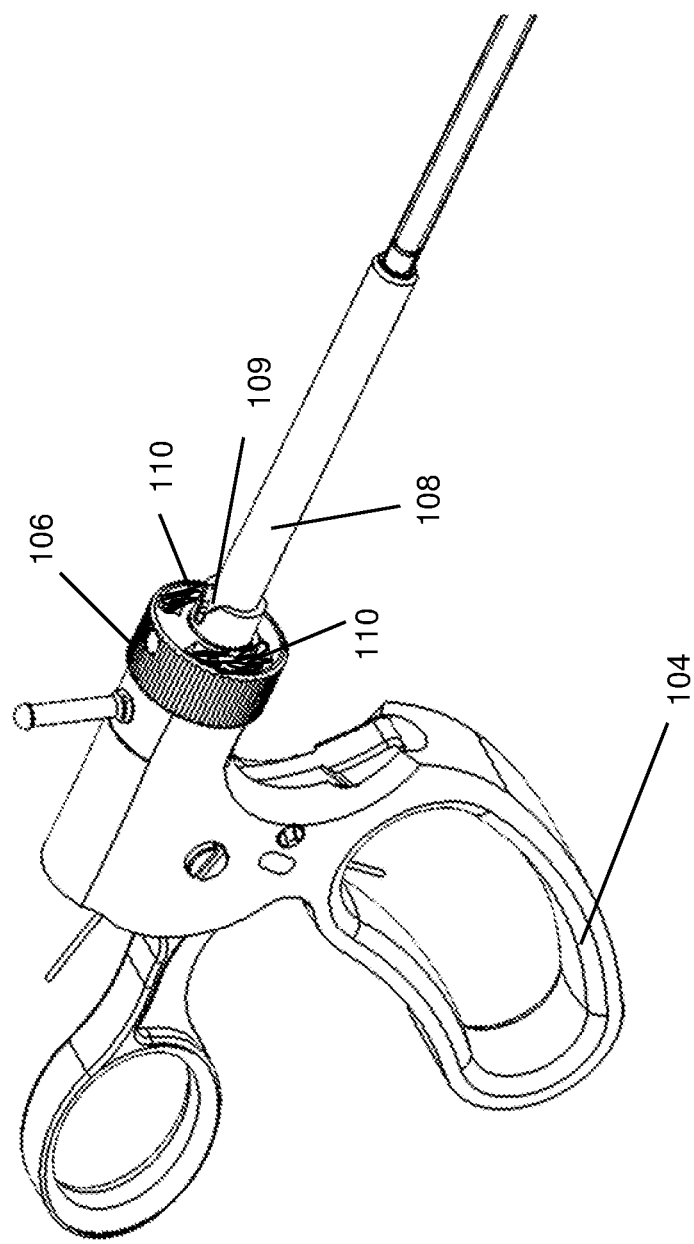
FIG. 11B is a perspective view of the handle and proximal shaft of the FIG. 11A instrument.

The user manipulates the handle 104 in an instinctive fashion, and in response the system causes corresponding movement of the instrument's distal end. The motors associated with the finger driver are energized in response to signals generated when the user moves the instrument handles side-to-side and up-down, resulting in motorized steering of the finger and thus the instrument's tip in accordance with the user's manipulation of the instrument handle. Combinations of up-down and side-side motions of an instrument handle will steer the instrument's tip within the body cavity up to 360 degrees. Manual rolling of the instrument handle about the instrument's longitudinal axis (and/or manually spinning of a rotation knob or collar proximal to the instrument handle) results in motorized rolling of distal part of the instrument's shaft 102 (identified in FIG. 11) using the roll driver 216.

Finger Drive Assembly

Figure 1C:
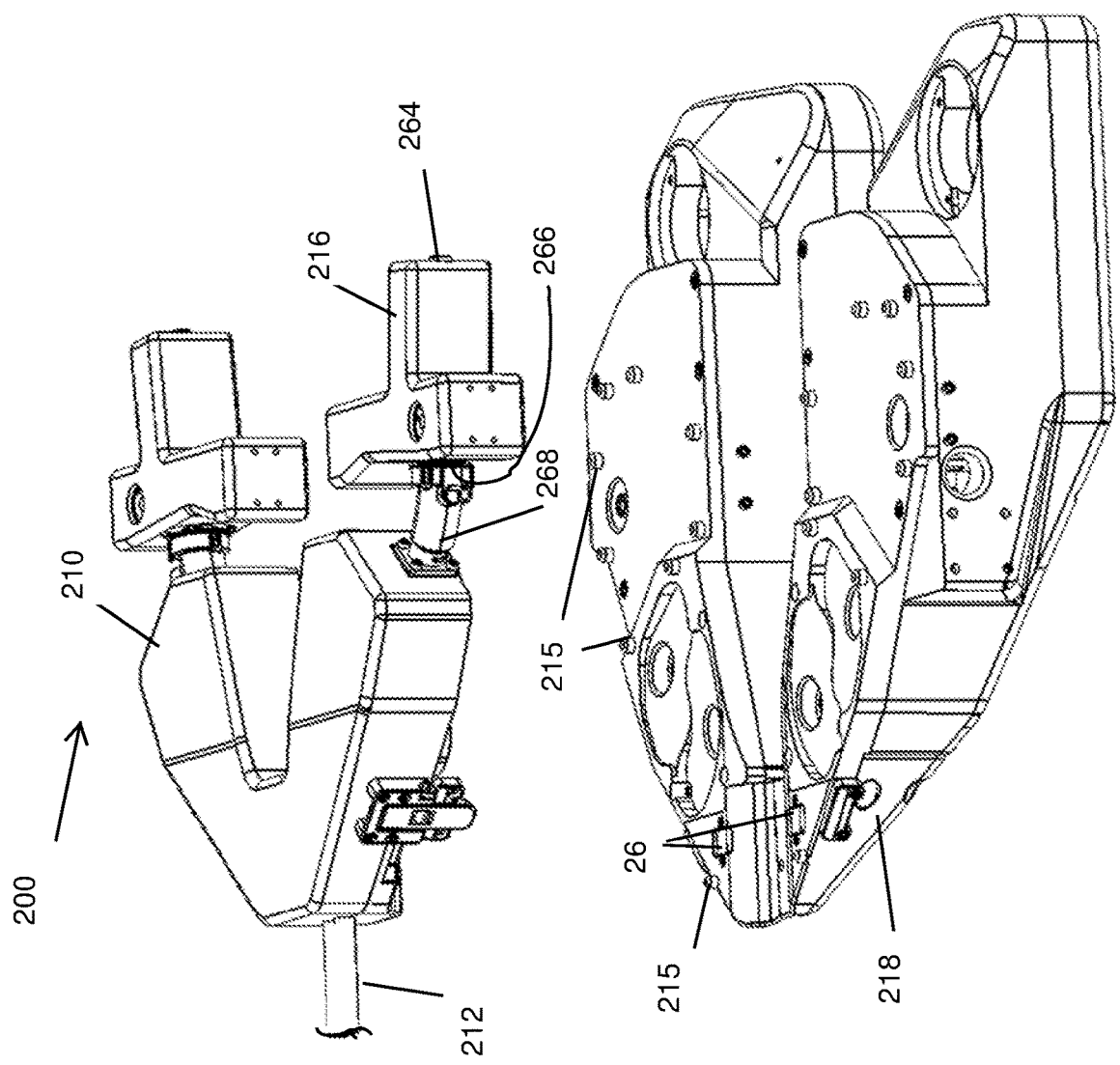
FIG. 1C is a partially exploded perspective view of the base unit, roll driver and finger drive assembly.
Figure 1D:
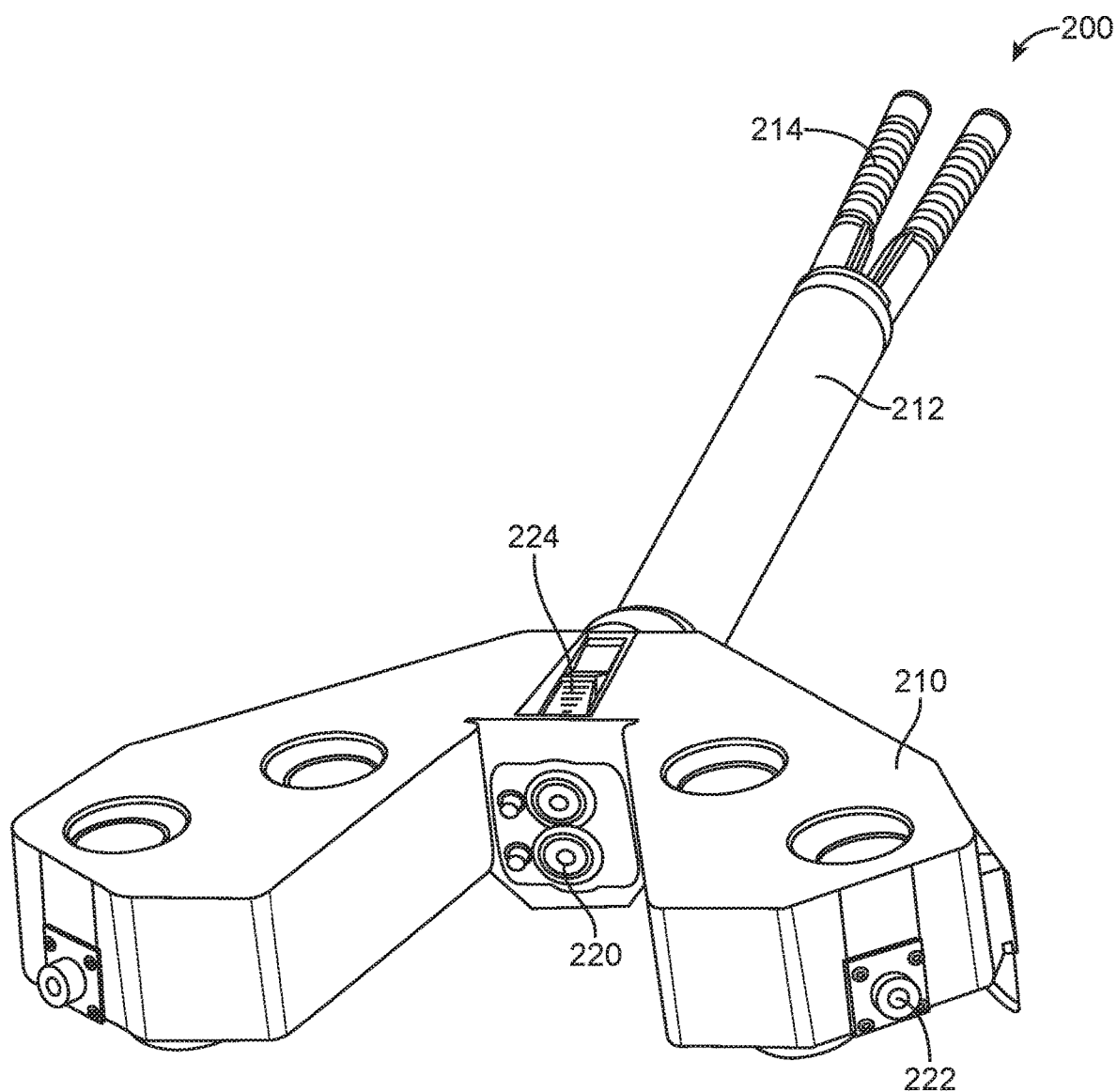
FIG. 1D is a perspective view of a proximal part of the finger drive assembly.

Referring to FIGS. 1A, 1C and 1D, the insertion tube 212 of the finger drive assembly 200 is an elongate tube positionable through an incision in a body cavity. The system is arranged such that multiple instruments may be introduced into the body cavity via the insertion tube. The illustrated embodiment allows for simultaneous use of three or four instruments—two that are actively steered using the tubular fingers 214, and one or two that enter the body via passive ports in the finger drive assembly 200. Different numbers of active channels (steerable fingers 214) and passive ports may instead be used in the system without departing from the scope of the invention. For example, an alternative system might include a single steerable finger 214 and no passive ports, or the illustrated system might be modified to add one or more steerable fingers 214 or to add or eliminate passive ports.

Deployment Mechanism

The finger drive assembly 200 has a deployment mechanism that is operable to simultaneously or independently reposition the distal portion of each finger 214 to increase or decrease its lateral separation from the longitudinal axis of the insertion cannula 212. The deployment mechanism moves the fingers 214 between an insertion position in which the fingers are generally parallel to one another for streamlined insertion, and one or more deployed positions in which the fingers are pivoted laterally away from the longitudinal axis of the insertion tube as shown in FIG. 1A. U.S. Publication Nos. US 2007-0299387 and US 2011-0230723 illustrate deployment mechanisms that can be used for the system 2.

Figure 2A:
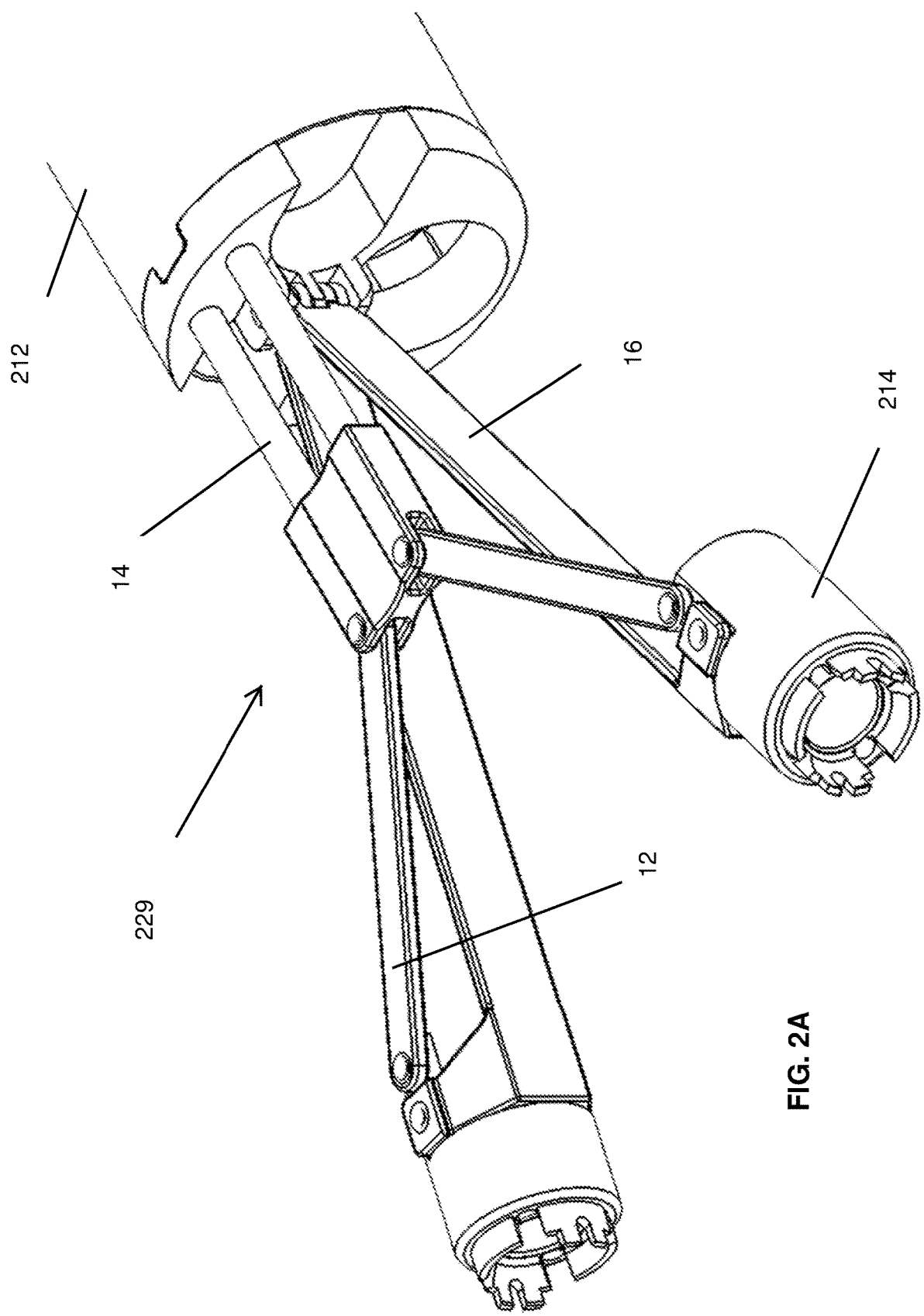
FIG. 2A is a perspective view of the distal portion of the deployment mechanism.

The first embodiment uses a deployment mechanism shown in FIG. 2A using pivotable links 12 for this purpose, with each link 12 pivotably coupled between a finger 214 (only a portion of which is shown in the figure) and one or more elongate members 14, which can slide relative to (and, in the illustrated embodiment, partially within) the insertion tube 212. Additional links 16 may extend between the distal end of the insertion tube 212 and the fingers 214, providing additional support for the fingers. In the drawings, these additional links 16 have a rectangular cross-section with their long edges oriented to resist bending when the fingers are loaded—such as when instruments in the finger are being used to grasp and elevate tissue. The proximal ends of the links 16 form a hinge coupled to the insertion tube as shown.

Figure 2B:
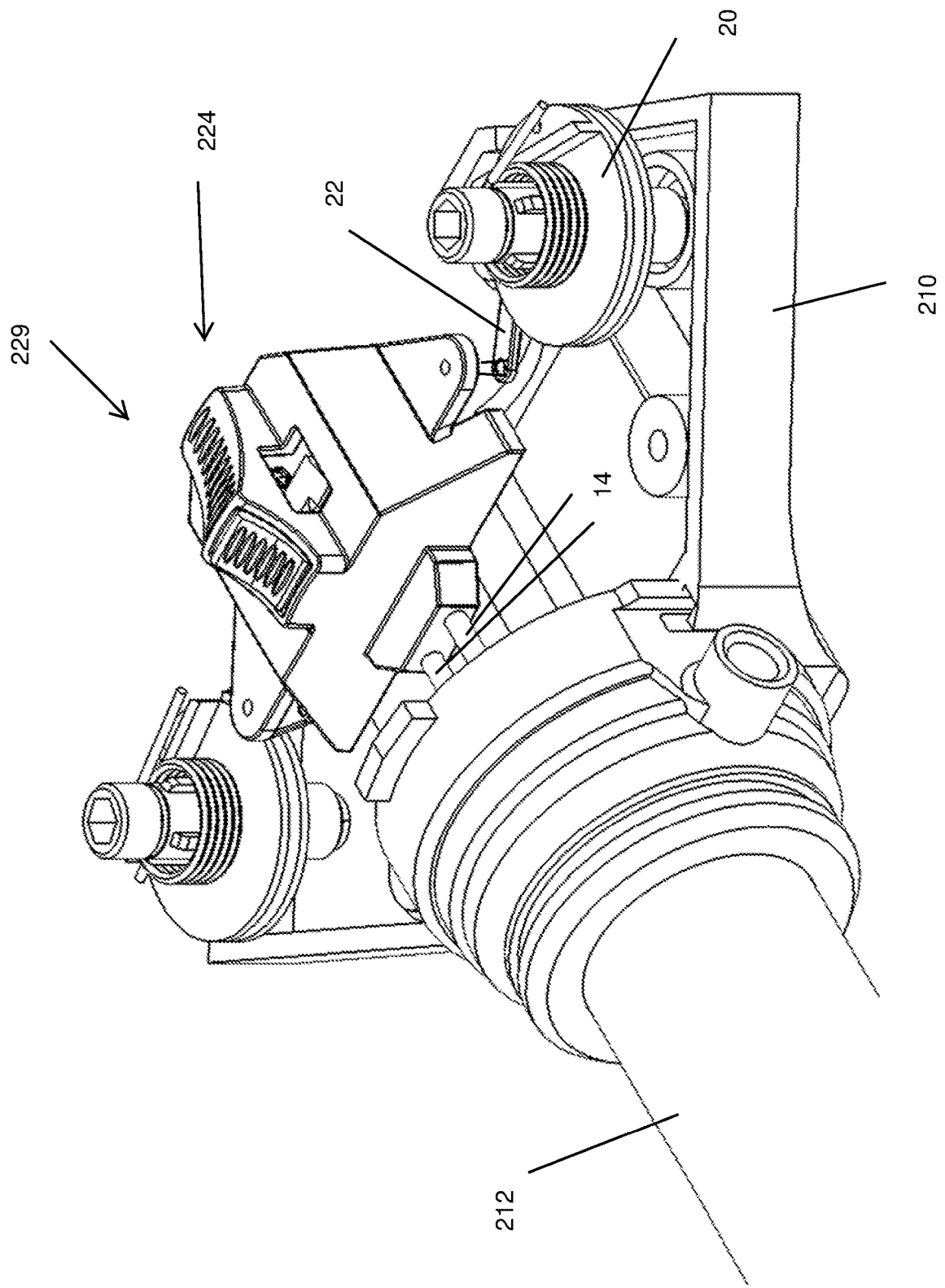
FIG. 2B is a perspective view of the proximal portion of the deployment mechanism.
Figure 2C:
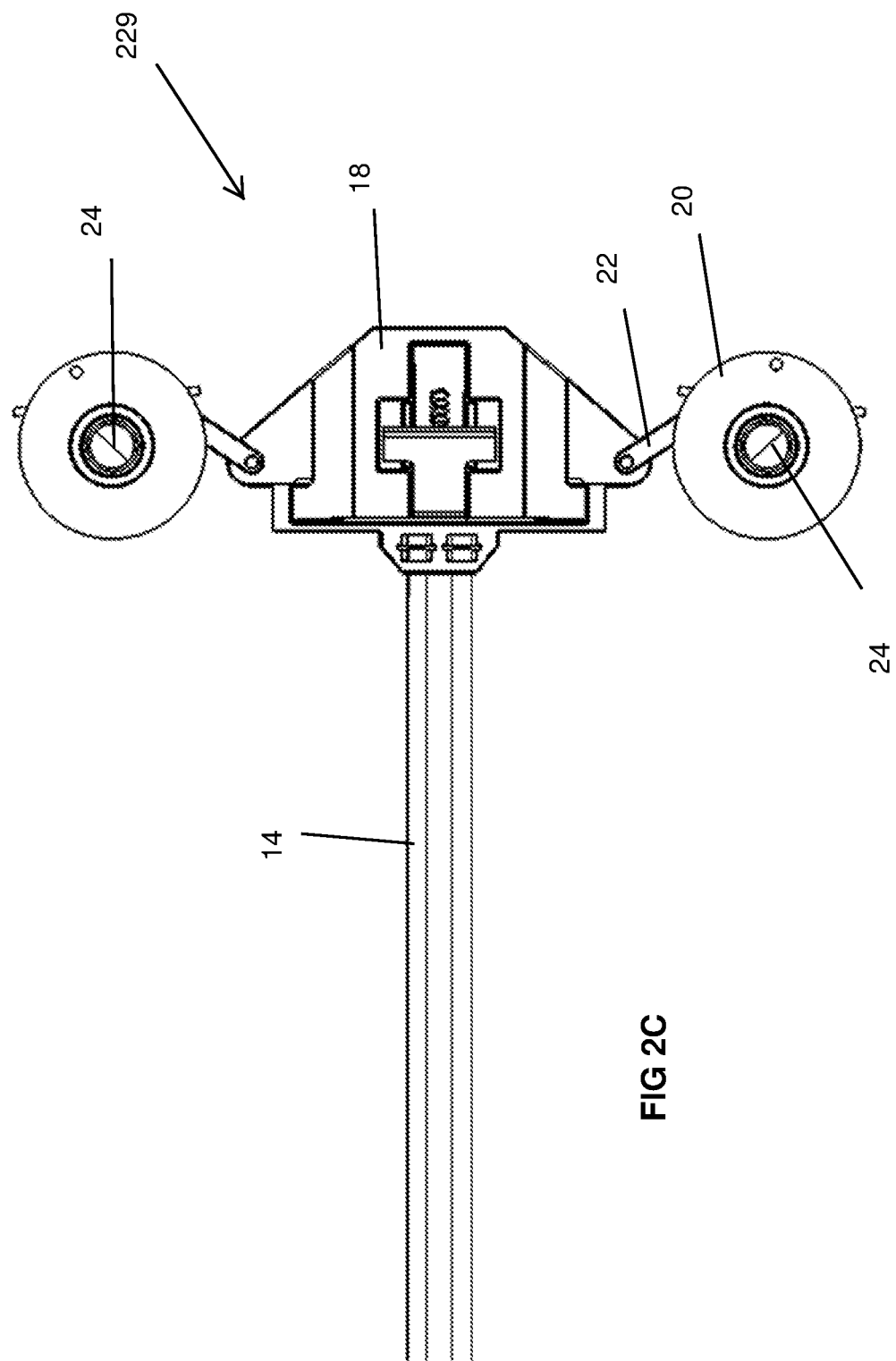
FIG. 2C is a plan view of the underside of the proximal portion of the deployment mechanism.
Figure 3:
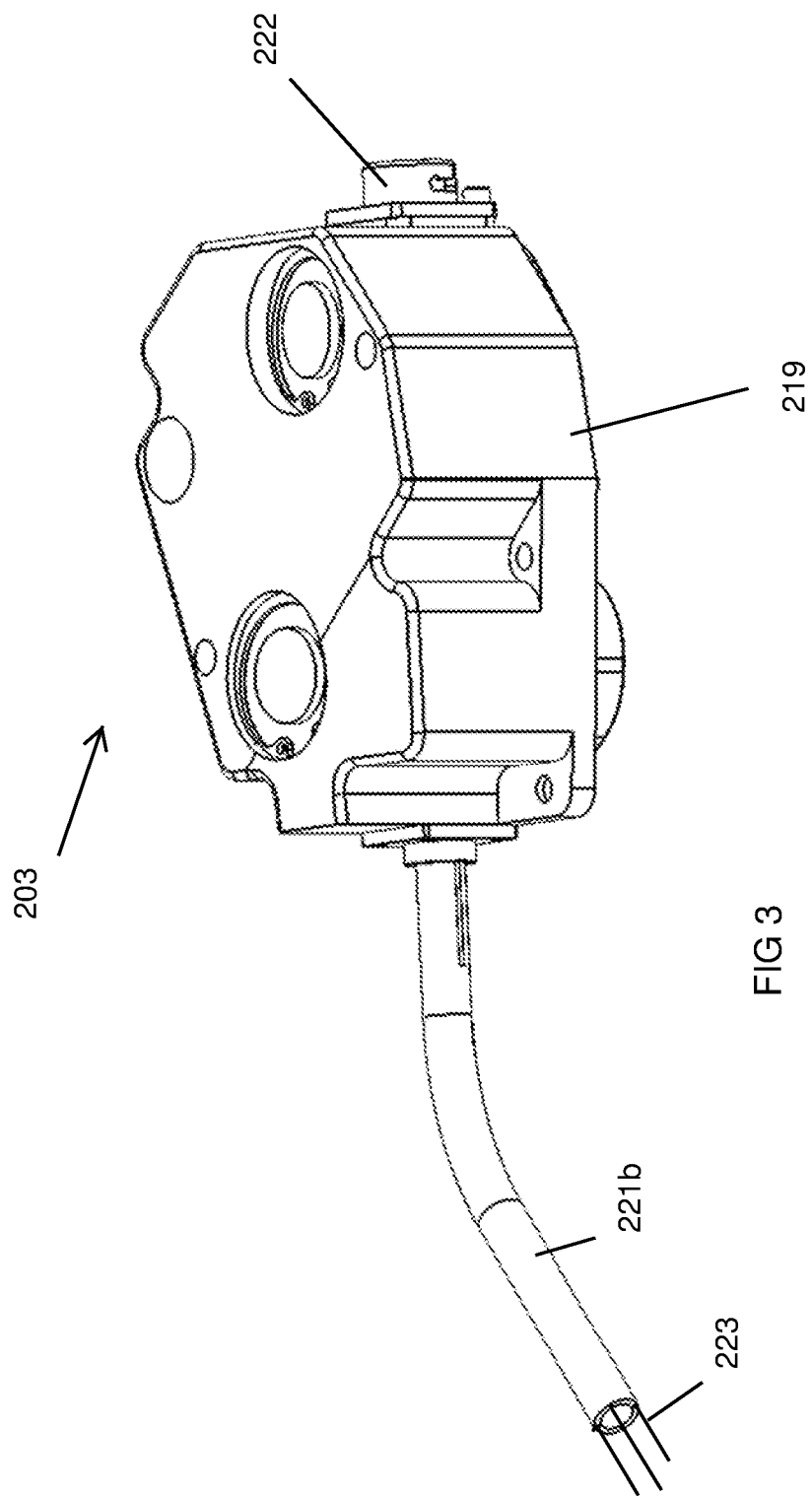

As shown in FIGS. 2B and 2C the proximal ends of the members 14 are connected to a block 18 moveable relative to the finger drive assembly's housing 210 between distal and proximal positions to slide the members 14 between distal and proximal positions. Sliding the members 14 in this way causes the link arms 12 to pivot and to thereby move the fingers laterally.

A ratchet feature 224 (FIG. 2B) is used to retain the longitudinal positioning of the block 18 relative to the housing 210 and to thereby maintain the fingers 214 in a selected deployment position. To deploy, and otherwise alter the lateral spacing of the fingers, the user disengages the ratchet and slides the block 18 proximally or distally to move the fingers from a first position to a second position. Re-engaging the ratchet causes the ratchet to engage the fingers in the second position. A spring (not shown) biases the ratchet in the engaged position. Other features relating to deployment and ratcheting are disclosed in US Publication No. US 2011-0230723.

The system 2 may include features that allow it to sense changes in the position of the deployment mechanism as an indicator of the finger's positions relative to the longitudinal axis of the insertion tube 212.

As shown in FIG. 2B, pulleys 20 are rotatably mounted on the housing 210. Each pulley 20 is coupled by a link arm 22 to the block 18, such that longitudinal movement of the block 18 to deploy the fingers 214 causes the pulleys 20 to rotate. At least one of the pulleys 20 includes a magnet 24 on its shaft, as shown in FIG. 2C, in which magnets 24 are shown positioned on the shafts of each pulley 20. The magnet 24 includes diametrically positioned north and south poles and preferably faces downwardly towards the base 218.

Encoder chips 26 (FIG. 1C) on a distal portion of the base 218 (FIG. 2) are positioned to align with the magnets 24 when the finger drive assembly 200 is mounted on the base 218. When the deployment mechanism is utilized, each encoder chips 26 senses the rotational position of the nearby magnet 24, which indicates the rotational position of the pulley 20 and thus the longitudinal position of the block 18. This information allows the system to know the state of deployment (i.e. the lateral or x-axis position) of the finger 214. Signals generated by the encoder chips 26 may be used by the system to coordinate proper transformation between a user's input instruction and the corresponding output commands.

In alternative embodiments, each finger may be independently deployed using a separately moveable sliding member 14, so as to allow each finger to be laterally repositioned independently of the other finger.

Although the first embodiment uses a manual deployment mechanism, in a modified system, one or more motors may be used to drive the deployment mechanism. In some such systems, motor-driven deployment might be performed independently of the steering of the fingers. In others, the system might dynamically control both the deployment mechanism and the finger drivers as a means to move the fingers into target positions and orientations based on the user's positioning of the instrument handles at the command unit 250. Control of the deployment mechanism and the finger drivers at a given point in time can be based on the calculated current position and orientation of the fingers using signals from the encoder chips 26 together with other sensed information described below.

Instrument Pathways

Referring to FIG. 1D, the finger assembly's housing 210 has a generally u- or v-shaped configuration, which each "leg" of the u- or v-shaped housing the finger drivers associated with a different one of the steerable fingers 214. While not a requirement, this shape leaves working space between the "legs" for additional instruments, as is discussed below.

Figure 15:
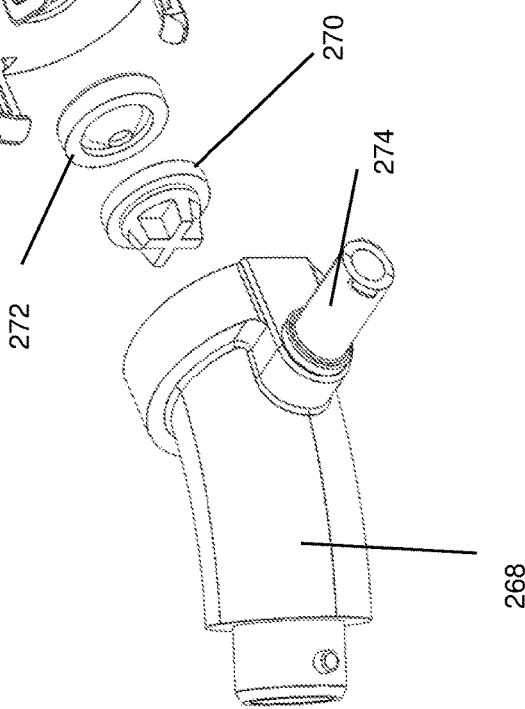

Ports 222 for the instruments 100 are positioned at the proximal end of each leg of the u- or v-shaped housing. These ports 222 may have seals disposed within the housing 210 to prevent loss of insufflation pressure through the ports 222 when no instruments are present in the ports and/or to seal around the shafts of instruments disposed in the ports. Additionally detachable seals may be placed proximal to the ports 222. One example of this configuration of seals is illustrated in FIG. 15.

Each port 222 defines the entrance to an instrument path through the housing 210 and insertion tube 212 into a corresponding one of the steerable fingers 214. The instrument path includes a tube or series of tubes extending from the port 222, through housing 210 and insertion tube 212, and out the distal end of the insertion tube 212 to form the finger 214. The instrument path 221 has a proximal tube 221a that extends distally from the port 222, and a distal tube 221b whose proximal end is positioned over the proximal tube 221a and whose distal end extends through the housing 210 and insertion tube 212. Central lumen in the proximal and distal tubes 221a, 221b are continuous to form the instrument path 221. The actuation elements or cables 223 used to steer the finger 214 extend through lumen in the distal tube 221b as shown.

Passive ports 220 (two are shown) are positioned to allow passage of additional instruments through the housing 210 and the insertion tube 212. In the drawings, these additional ports 220 are shown positioned in the crotch of the u- or v-shaped housing 210. These ports allow instruments such as scopes, rigid instruments and other instruments to be passed through the insertion tube and used simultaneously with the instruments deployed through the steerable fingers 214. Seals (not shown) in these ports 220 are positioned to prevent loss of insufflation pressure through the ports when no instruments are present in the ports, and also to seal around the shafts of instruments disposed in the ports 220.

Finger

Referring again to FIG. 1, each finger 214 includes a deflectable distal portion 216, which may be formed of a plurality of vertebrae or links as shown, or flexible tubing, slotted or laser-cut metal tubing, or other materials capable of being steered without kinking or buckling. Examples of steerable channels that may be suitable for use as steerable finger 214 are shown and described in US 2011/0251599 and the other applications referenced herein. A flexible sleeve/liner (not shown) covers the deflectable distal portion 216 to avoid capture of tissue in gaps between vertebrae or slots.

The distal end of each the finger 214 may be equipped with a telescoping reinforcement feature positioned on its distal end such that as an instrument tip exits the distal end of the finger, the reinforcement expands distally in a longitudinal direction—surrounding the portion of the instrument tip that extends beyond the end of the finger 214. This feature helps support any portion of the instrument shaft that extends beyond the distal end of the finger 214, thus avoiding undesirable flexing of the instrument shaft within the body cavity.

The fingers 214 are steered through selective pulling and/or pushing of the actuation elements 223 (e.g. wires, cables, rods, etc). In this description the term "cable" will be used to represent any such type of actuation element. The cables 223 are anchored at the distal end portions of the steerable fingers 214 and extend proximally through the steerable fingers 214 into the housing 210. The number of cables to be used in a steerable finger may vary. For example, each steerable finger may include two or four cables, wherein distal portions of the cables are arranged 180 or 90 degrees apart, respectively, at the distal end of the finger. In other embodiments, three cables may be used for each finger.

In the illustrated embodiment four cables are used. By "four" actuation cables it is meant that there may be four separate cables/wires etc or two cables/wires each of which has a U-turn anchored at the distal end of the finger such that four cable proximal ends are disposed within the housing 210. Additional cables that are not used for actuation may be positioned through the fingers and used to provide feedback as to the position of the tips of the corresponding fingers, using methods to those similar to those described below.

Finger Driver

This section describes the finger driver for one of finger 214 shown in FIG. 1A. It should be understood that the steerable finger shown on the right side is manipulated using a finger driver having similar features.

The proximal end of each cable 223 extends out of the proximal end of the tube 221b and is engaged to a pulley 232a or 232b. Each pulley 232a, 232b includes a spur gear 231a, 231b as shown. While the drawings show the axes of rotation of the 232a, 232b pulleys to be non-parallel relative to one another, in other embodiments the pulleys may be oriented to have parallel axes of rotation.

A first pair of the pulleys 232a is engaged to two cables 223 that are anchored at points separated by 180 degrees at the distal end of the corresponding steerable finger. The components in the finger drivers are arranged so that each steering motor in the base unit drives one such pair of the cables—although in other embodiments each cable has a dedicated steering motor. To allow each steering motor to drive two cables, each finger driver 203 is arranged with a first gear 230a disposed between and engaged with the teeth of the gears 231a on the first pair of pulleys 232a, such that rotation of the gear 230a in a first direction (by action of a steering motor as is discussed below) tensions one cable in the pair and reduces tension on the other cable in the pair, thus deflecting the distal end of the corresponding steerable finger in a first direction. Similarly, rotation of the gear 230a in the opposite direction (by reversing operation of the corresponding steering motor) deflects the distal end of the steerable finger 214 (not shown) in the opposite direction by tensioning the opposite cable. A second pair of the pulleys 232b is similarly driven by a second gear 230b disposed between and engaged with the teeth on the gears of the second pulleys 232b. The cables associated with the second gear 230b are also preferably arranged 180 degrees apart at the distal end of the steerable finger (and offset 90 degrees from the cables associated with the first gear 230a) allowing for 360 degrees of deflection of the steerable finger 214.

The pulleys 232a, b and gears 230 a, b are housed within a sealed pulley box 219. The proximal end of the tube 221b and the full length of the tube 221a (FIG. 4) are housed within the sealed box 219. Each pulley box is mounted within the housing 210 of the finger drive assembly 200 and oriented with the port 222 exposed at the proximal end of the housing 210 and with the tube 221*b* extending into the insertion tube 212. Seals surround the port 222 and tube 221*b* to seal the pulley box against passage of moisture and contamination into the space surrounding the gears and pulleys during cleaning.

Figure 5A:
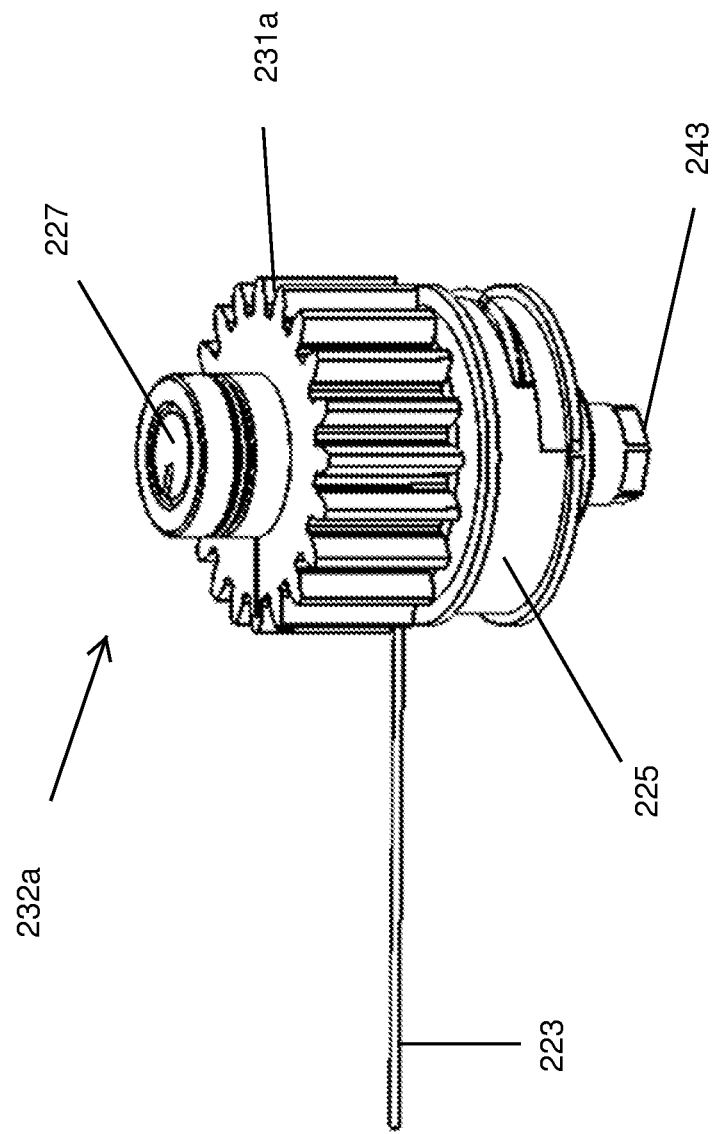
FIG. 5A shows a pulley of a finger driver.

FIGS. 5A-5C show one embodiment of a pulley 232*a*. Each such pulley includes a spool 225 rotationally fixed to a shaft 227. Gear 231*a* is positioned on the shaft 227 and can spin relative to the shaft 227. The pulley 232*a* is sprung by a coil spring 229 disposed around the shaft, with one end of the spring 229 attached to the gear 231*a* and the other end attached to the spool 225. The spool includes a pair of posts 235 spaced 180 degrees apart. The gear has a pair of stops 237 spaced 180 degrees apart and separated by an annular space 241. The posts 235 of the spool 225 extend into the annular space 241.

The cable 223 is wound on the spool 225. Each pair of the cables is tensioned such that when a finger is in a straight orientation as schematically shown in FIG. 6A, each post 235 is positioned against one of the stops 237. When a motor is used to drive the pulleys to bend the finger to the left as shown in FIG. 6B, the gear 231*a* of the pulley 232*a* on the left spins in a clockwise direction, and as it spins its stops 237 remain in contact with the posts 235 of the corresponding spool—thus the gear and spool move as a solid body. Rotation of the spool tensions the cable 223L, causing the finger to bend to the left as schematically shown. At the same time, the gear of the pulley 232*a* on the right spins in a counter-clockwise direction and the cable 223R slackens due to compliant members of the cable transmission and body. As the gear spins, its stops 237 rotate away from the posts 235 of the corresponding gear. Because the gear 231*a* and spool 225 are connected by the spring 229 (FIG. 5C), the spring force eventually acts on the spool to rotate it counter-clockwise, thus taking up extra slack in the cable 223R.

Output from sensors associated with the pulleys is used to calculate the position of the tips of the fingers, force on the cable or finger tip by extension, and to provide redundant sensing of the position of the finger tip relative to that sensed by the motor's encoder. The following discussion of the use of the sensors will focus on the situation in which a finger is pulled to the left as in FIG. 6B, but it should be understand that the same principles apply for each direction in which the finger is steered.

In general, the system makes use of the passive cable in each cable pair (a cable pair being a pair of cables tensioned by a common one of the gears 230*a*, 230*b*) to provide positional feedback corresponding to the position of the tip of the corresponding finger. Referring to FIGS. 4B and 5A, each pulley 232*a*, 232*b* has disk magnet 243 having a distally-facing surface having diametrically positioned north and south poles. Encoder chips 245 in the base unit 218 (FIG. 8A, discussed below) are positioned to detect the rotational position of each such magnet. When the finger is steered to a bent position, such as the left-ward bend in FIG. 6A, the cable 223L tensioned to produce the bend undergoes elastic stretching under load, and also deforms the shaft of the tubular passage 221 through which the cable extends. Thus the distance that cable 223L was withdrawn to cause the bend does not correspond directly to the amount by which cable 223R has advanced in response to bending. Since the passive cable 223R is not under the high loads being experienced by the active cable, the distance that the passive cable 223R advanced (as indicated by the degree of rotation of the magnet 243 sensed by the encoder chip), reflects the amount by which the finger is bent and can be used by the system to derive a more accurate measurement of the position of the finger in three dimensional space. This system is beneficial in that it eliminates the need for a cable, pulley and sensor arrangement devoted solely position sensing.

Moreover, the difference between the amount by which the active cable 223L was withdrawn and the passive cable 223R advanced represents the amount of force applied by the active cable 223L at the instrument tip. While feedback as to the force at the tip also comes from measuring current on the steering motors, the force at the tip provides a more direct measure of the force.

Feedback from the motor's encoder can be compared with the positional information obtained from the magnet associated with cable 223L and used to detect whether there is an error in the system. For example, if the position measured at the motor is significantly different from the position derived from the positions of the magnets 243, the system might alert the user to the possibility that the active cable 223L is broken and disable the system 2.

If the pulley associated with an active cable is determined to have rotated out of its normal range of motion to its extreme relaxed position (e.g. to a position against the stop 237 opposite to the stop it should be positioned against in order to be driven by the gear), it will indicate an error in the system that might potentially be an error in the system. Feedback indicating that both pulleys in a pulley pair are in a relaxed state, or have both rotated to a position against a stop when one of the cables is tensioned, is indicative of a broken cable. When error conditions are detected the system, the system may disengage the motors and deliver an error message to the user via the computer interface 201.

Motion Transfer—Base Unit to Finger Drivers

The finger driver 203 receives motion from the steering motors 236*a, b* in the base unit 218 through rotational coupling between elements on the finger drive assembly and elements on the base 218. On the finger drive assembly 200, members such as driven shafts 226*a*, 226*b* (FIG. 7A) are exposed on the bottom of the housing 210. Each of the driven shafts 226*a*, 226*b* is rotationally fixed to and axially aligned with the one of the gears 230*a*, 230*b* (FIGS. 4A and 4B) within the housing 210, such that rotating each driven shaft 226*a*, 226*b* rotates the corresponding gear 230*a*, 230*b*, thus steering the steerable finger 214 as described above. The driven shafts 226*a*, 226*b* may extend from or be recessed at the lower surface of the housing 210.

Figure 7A:
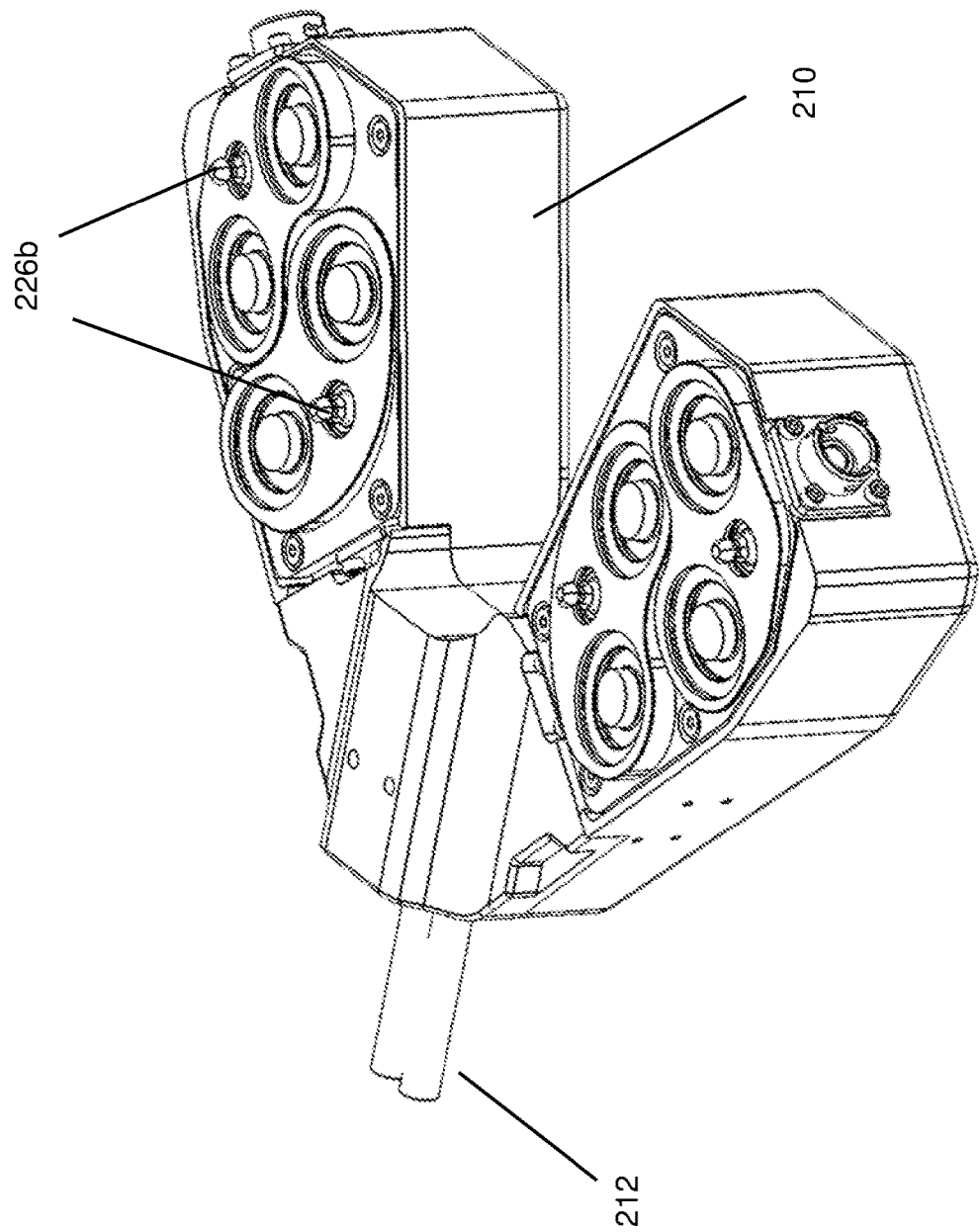
FIG. 7A is a perspective view showing the underside of the finger drive assembly.
Figure 7B:
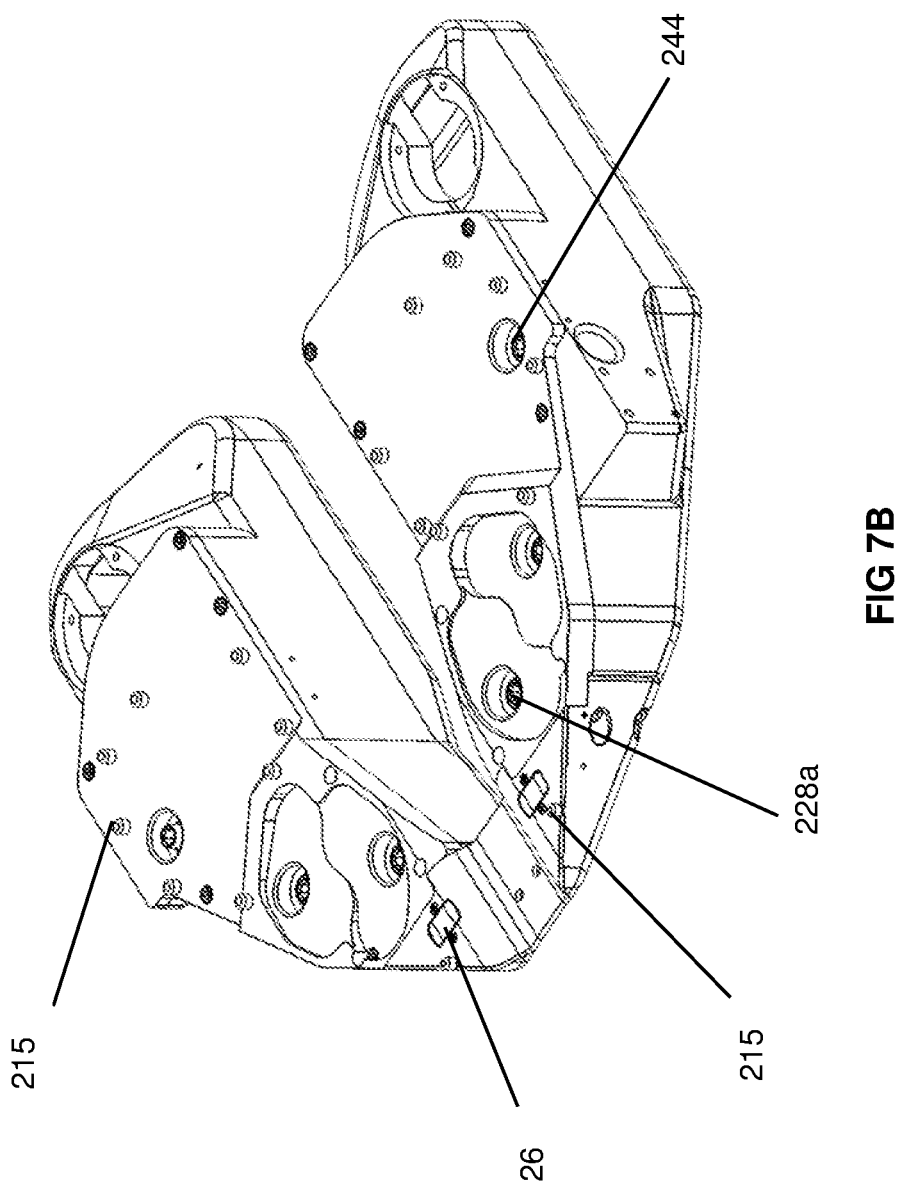
FIG. 7B is a perspective view showing the top side of the base unit.

As shown in FIG. 7B, second members such as drive shafts 228*a*, 228*b* are exposed at the upper surface of the base 218 and may extend from or be recessed at the upper surface of the base 218. Each drive shaft 228*a*, 228*b* is releasably engageable with a corresponding one of the driven shafts 226*a*, 226*b* on the bottom of the housing 210 (FIG. 7A). Driven shafts 226*a*, 226*b* (FIG. 7A) and drive shafts 228*a*, 228*b* (FIG. 7B) are designed for mating engagement or any alternative form of engagement that will allow for the transmission of torque from each drive shaft to its corresponding driven shaft. In the arrangement shown in the drawings, driven shafts 226*a*, 226*b* are male components that mate with drive shafts 228*a*, 228*b* as their female counterparts. The illustrated male components include hex ball heads of spherical hex keys and the female components include hex sockets for receiving the hex heads. In this embodiment the rotational axis of each first member 226*a*, 226*b* angularly intersects the rotational axis of the corresponding drive shaft 228*a*, 228*b*. In other embodiments, however each first member might share a common rotational axis with the corresponding drive shaft.

While the driven shafts and drive shafts are shown as hex mating pieces, any alternative engagement features that will likewise allow transmission of torque from the drive shafts 228a, 228b to the driven shafts 226a, and 226b can instead be used.

To facilitate engagement between the drive shafts 228a, b and the driven shafts 236a,b, the drive shafts 228a,b are downwardly displaceable into the base unit 218 when first contacted by the driven shafts 226a,b. Springs bias the drive shafts 228a, b in their outermost position, so that they will spring upwardly once mating features of the drive shafts 228a, 228b and driven shafts 226a, 226b engage. Sensors may be positioned in the base unit 218 to sense when each shaft has returned to its fully extended position, allowing the system to know whether any of the drive shafts 228a has not properly engaged with the corresponding driven shaft 226a. This sensed information may be used to lock out use of the system until all shafts are properly engaged. It can also be used to initiate minor rotation of the steering motors associated with the shafts 228a that have not sprung upwardly, to allow the hex head of the shaft 228a to move to an orientation where it will engage with the hex socket of the corresponding shaft 226a.

As will be evident from the following section, engaging the driven shafts and drive shafts allows for the transfer of motion from the system's steering motors to the pulleys that manipulate the cables for steering the fingers.

Base Unit

The base unit 218 houses steering motors 236a, b and a roll motor 238. The illustrated system has a u- or v-shaped configuration similar to that of the housing 210. The base unit 218 is organized such that motors associated with steering the left-side finger 214 and with axially rolling an instrument extending through the left-side finger 214 are in the left side of the base unit 218 (e.g. in the left leg of the v- or u-shaped housing), and such motors associated with the right-side finger and its instrument are in the right side of the base unit. The computer controllers, motor drivers, and associated electronics for each side of the system are also housed within the base unit 218. In this embodiment, two computer controllers/real time processors are included in the base unit 210, each associated with one of the fingers, although in other embodiments a single real time processor may be associated with both fingers. Communication between these computers and the user interface computer (e.g. touch screen computer 201 of FIG. 1A) may use an ethernet TCP/IP connection through a router, or other means. In other embodiments, a touchscreen processor and real time processor are housed within a single computer, eliminating the need for the router.

Figure 8A:
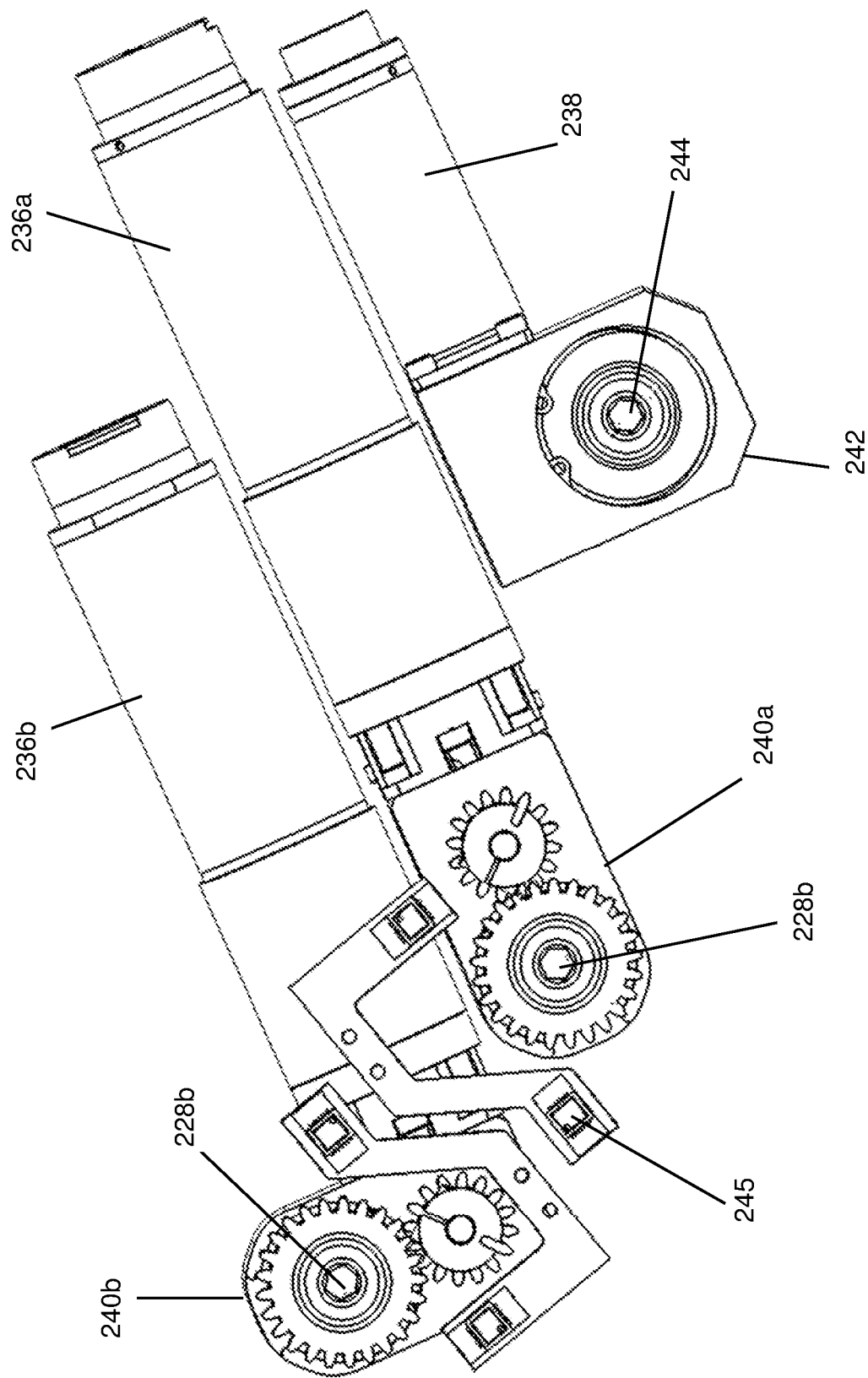
FIG. 8A is a plan view showing the layout of the motors, sensors and gear assemblies within one half of the base unit.
Figure 8B:
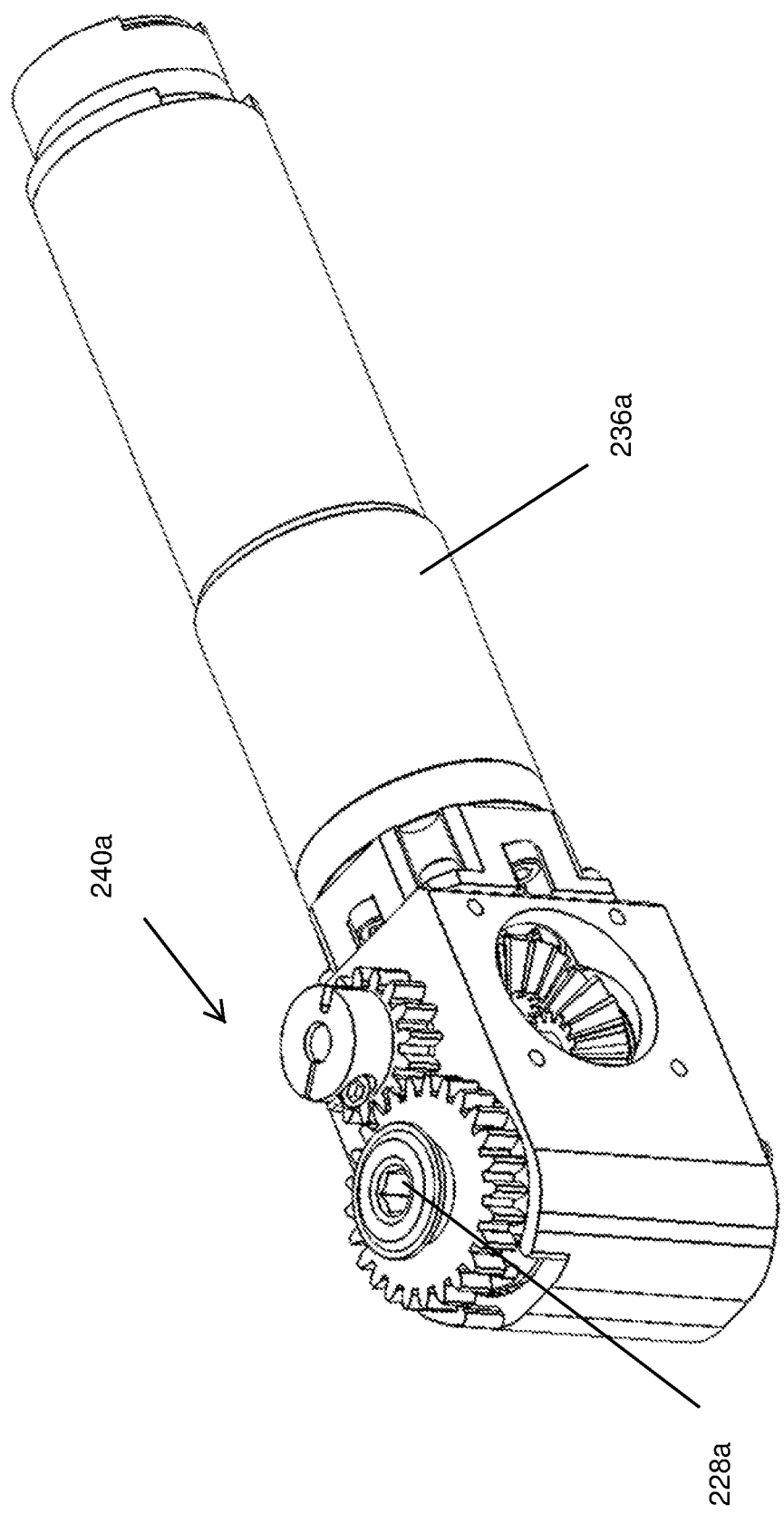
FIG. 8B is a perspective view of one of the motors and gear assemblies from FIG. 8A.

FIG. 8A shows an arrangement of the motors 236a, b, 238 and their corresponding gear assemblies within the base unit's housing (not shown). Each steering motor 236a, b housed within the base 218 drives the gears of its corresponding gear assembly 240a, b.

A gear in each gear assembly 240a, 240b is rotationally fixed to one of the exposed drive shafts 228a, 228b so that activation of the motors 236a,b produces axial rotation of each of the drive shafts 228a, 228b. Two such steering motors 236a, b, are shown for each finger, each with a corresponding gear assembly 240a, b. Motor 236a is positioned to drive gear assembly 240a to produce axial rotation of drive shaft 228a. Motor 236b drives gear assembly 240b to produce axial rotation of drive shaft 228b.

Referring again to FIG. 8A, the output of roll motor 238 in the base unit is coupled by way of gear assembly 242 to a member such as a roll driving shaft 244, so as to cause axial rotation of the roll member 244 when the roll motor 238 is operated. The roll driving shaft 244 may be similar in configuration to the drive shafts 228a, 228b.

Roll Driver

Figure 9:
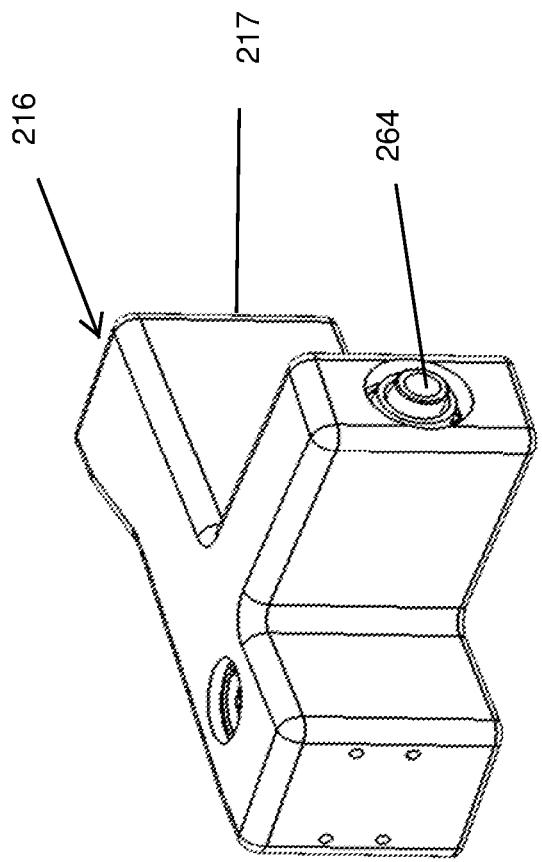
Figure 10:
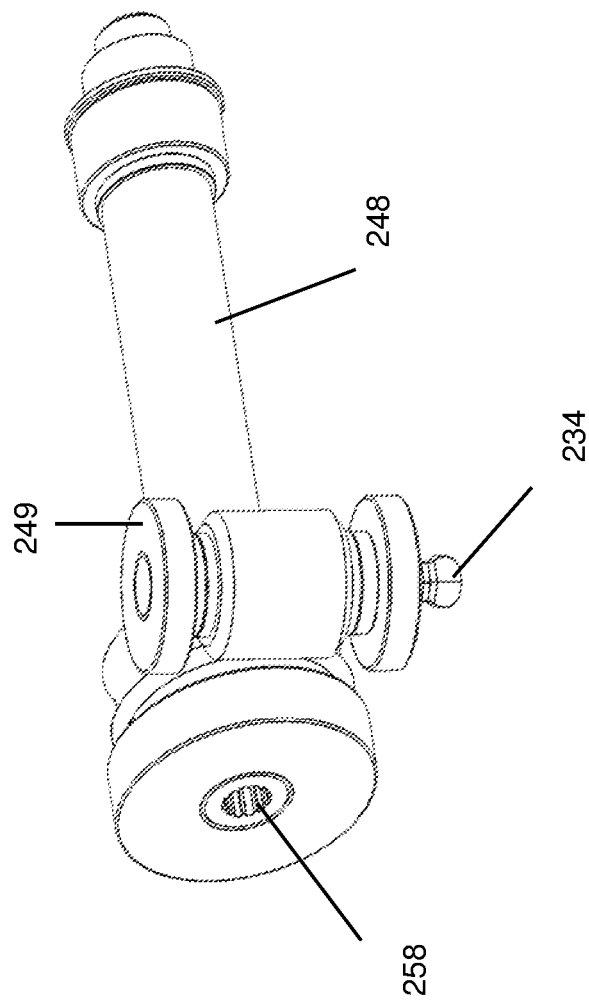

The roll driver 216 (FIGS. 1A, 1B and 9) includes a housing 217. As shown in FIG. 10, a roll drive tube 248 is axially rotatable within the roll driver housing 217 (not shown in FIG. 10). Roll drive tube 248 includes a lumen for receiving a portion of the shaft of instrument 100 (FIG. 1A). The exterior of the roll drive tube 248 forms a worm gear, which engages with a roll gear assembly that includes an adjacent worm gear 249. The roll gear assembly includes a member such as driven roll shaft 234 that is exposed at the lower surface of the housing 217 (not shown). The driven roll shaft 234 is axially rotatable relative to the roll driver housing 217.

The roll driver 216 is positionable on the base unit 218 such that the driven roll shaft 234 rotationally engages with the roll driving shaft 244 (FIG. 7B) of the base unit 218. This rotational engagement allows transfer of torque from the shaft 244 to the shaft 234—thus allowing rotation of the roll drive tube 248 (and thus the instrument shaft) through activation of the roll motor 238. The shafts 234, 244 may be mating pieces similar to those described for the driven shafts and drive shafts 226a, b and 228a, b used for steering.

The roll drive tube 248 has features designed to rotationally engage with corresponding features on the surgical instrument shaft. This engagement allows axial rotation of the roll drive tube 248 to produce axial rotation of the distal portion of the instrument shaft. Preferred features are those that create rotational engagement between the instrument shaft and the roll drive tube 248, but not sliding or longitudinal engagement. In other words, the features are engaged such that axial rotation of the roll drive tube 248 axially rotates the instrument shaft, but allow the instrument to be advanced and retracted through the roll drive tube 248 for "z-axis" movement of the instrument tip. Rotational engagement between the instrument shaft and the roll drive tube 248 should preferably be maintained throughout the useful range of z-axis movement of the instrument tip (e.g. between a first position in which the instrument tip is at the distal end of the finger to a second position in which the instrument tip is distal to the distal end of the finger by a predetermined distance.)

Figure 12B:
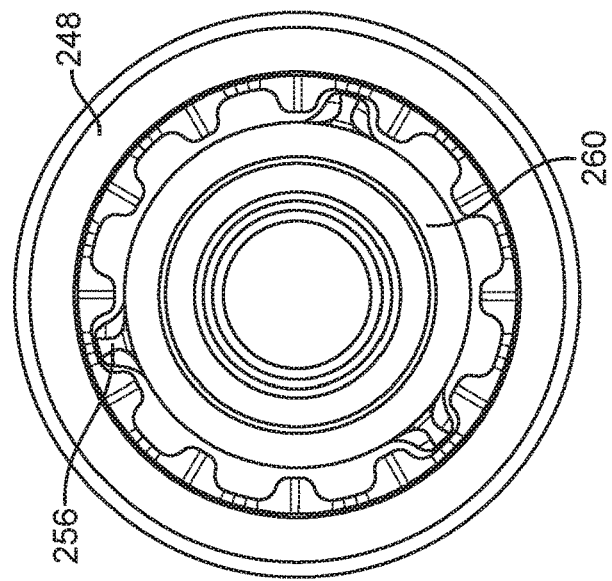
FIG. 12B shows the drive segment of FIG. 12A positioned within the roll drive tube.
Figure 12A:
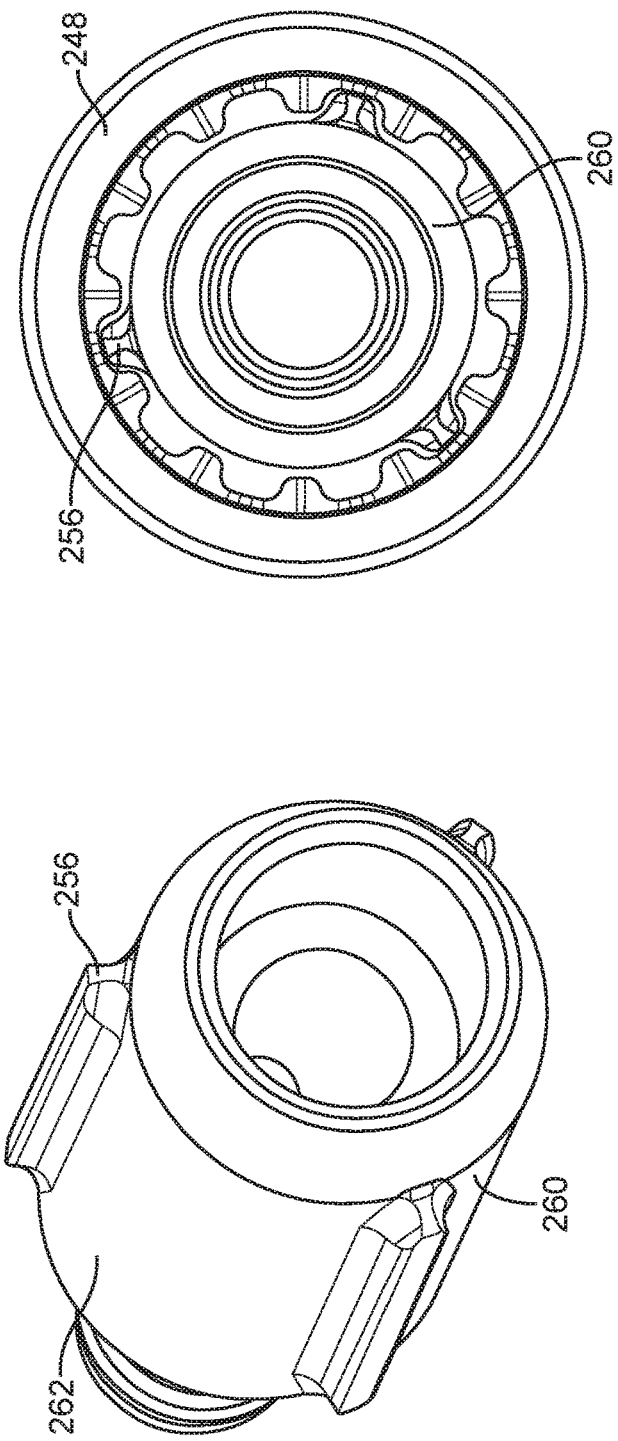
FIG. 12A is a perspective view of the drive segment of the instrument of FIG. 11A.

Engagement features for the instrument 100 and roll drive tube 248 include first surface elements on a drive segment 260 of the shaft 102 of the instrument 100 (FIG. 11) and corresponding second surface elements on the inner surface of the roll drive tube 248 (FIG. 10). Examples of surface elements 256, 258 are shown in FIGS. 12A-14. Referring to FIGS. 12A and 12B, the drive segment 260 of the instrument shaft 102 includes first surface elements 256 in the form of splines or ribs extending radially from the instrument shaft and longitudinally along the shaft. The lumen of the roll drive tube 248 includes second surface elements 258 in the form of longitudinally extending ribs (also visible in FIG. 12B). The surface elements 256, 258 are positioned such that when the roll drive tube 248 is rotated, second surface elements 258 on the interior lumen of the roll shaft contact and cannot rotationally bypass the surface elements on the instrument shaft. The distal ends of the splines 256 may be tapered such that they are narrower (in a circumferential direction) at their distal ends than they are further proximally, to facilitate insertion of the splines/ribs between corresponding ones of the ribs while minimizing play between the splines 256 and adjacent ribs 258 as the roll shaft rotates the instrument shaft. The longitudinal length of the splines 256 is selected to maintain rotational engagement between the instrument shaft and the roll shaft throughout the desired z-axis range of motion.

The drive segment 260 of the instrument shaft may have a larger diameter than proximally- and distally-adjacent sections, as shown in FIG. 11. To facilitate insertion of the drive segment 260 into the roll drive tube 248, the drive segment 260 includes a chamfered distal edge 262.

As another example, shown in FIGS. 13A-13C, the drive segment 260 has a hexagonal cross-section and the roll drive tube 248 has longitudinal grooves with v-shaped radial cross-sections as shown. Edges 256a of the drive segment 260 formed by corner regions of the hexagonal cross section seat in troughs 258a so as to permit longitudinal sliding of the instrument through the lumen but prevent rotation of the instrument within the lumen.

Figure 14:
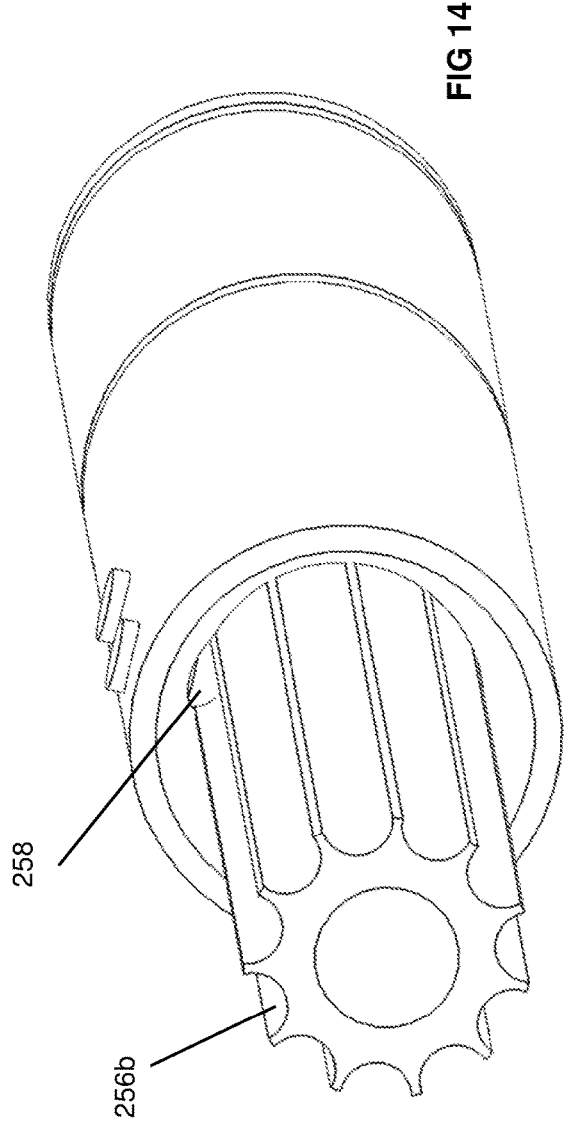

In another embodiment shown in FIG. 14, drive segment 260 includes longitudinally extending grooves 256b. One or more pins 258b extend radially inwardly from the luminal wall of the roll drive tube 248 and into engagement with one of the grooves 256b.

It should be noted that the instrument 100 is preferably constructed so that the roll drive tube 248 will cause rolling of the drive segment 260 and all portions of the instrument shaft 102 that are distal to it (including the end effector), without causing axial rolling of the instrument handle 104. Thus the handle and shaft are coupled together in a manner that permits the instrument shaft to freely rotate relative to the handle when acted upon by the roll drive tube 248. For example, the instrument 100 might includes a roll joint within, or proximal to, the drive segment.

Tubular Connectors

Openings 264 and 266 (FIG. 1C) at the proximal and distal surfaces of the roll driver housing 217 allow passage of an instrument shaft through the lumen of the roll drive tube 248. If, as in the first embodiment, the finger drive assembly and the roll drivers are separate components, any gap between the components is bridged by a tubular connector 268 mounted between the distal opening 266 of the roll driver housing 217 and the proximal port 222 of the housing 210 so as to provide a continuous instrument path. The tubular connector 268 can be removably connected to the roll driver housing 217 and the housing 210, or it might be more permanently connected to one or both of them. There may also be a similar tubular connector between the instrument box 252 and opening 264 on the roll driver to guide the instrument shaft into the roll driver.

Referring to FIG. 15, the tubular connector 268 may include a luer port 274 for use as a flush port or for directing insufflation gas through the finger drive assembly 200 and into the body cavity. A valve 270 such as a cross-slit valve is positioned within the tubular connector 268 to prevent loss of insufflation pressure through its proximal end, when no instrument is present. A second seal 272 is positioned to seal against the shaft on an instrument that passes through the tubular connector, thus minimizing loss of pressure around the shafts of an instrument disposed through the connector 268. In other embodiments, the luer port 274, valve 270, and seal 272 may be disposed in the housing 210. A single seal, or other seal configurations may also be utilized to seal with and without an instrument present.

Command Interface

Referring again to FIG. 1A, the base unit includes a command interface 250 equipped to generate signals corresponding to the position of, and/or a change in the position of, a proximal part of the surgical instrument 100 when the handle 104 is manually moved by a user (as well as other signals discussed below). The system generates control signals in response to the signals generated at the command interface. Such control signals are used to drive the motors 236a, b, 238 to steer the fingers and roll the instrument's shaft in accordance with the user's manipulation of the instrument handle. Thus, manual movement of the instrument handle by the user results in motor driven steering of the instrument's distal end and motor driven axial roll of the instrument shaft.

In this embodiment, it is the instrument's handle 104 (FIG. 1) whose movement triggers the signals of the command interface that result in steering of the fingers and rolling of the instruments. In other embodiments, a proximal portion of the instrument shaft, or another component of the instrument can be used. Still other embodiments use a separate user input device to generate the signals inputting the desired position of the instrument, rather than user input devices that respond to the user's movement of the instrument handle itself.

Turning to FIG. 16, the command interface 250 includes a first portion or bracket 276a that is anchored to the base 218 (not shown) and rotatable about an axis A1 (which may be generally normal to the surface of the base). A second portion or bracket 276b is mounted to the first bracket 276a and is rotatable about axis A2 (which may be generally parallel to the surface of the base and perpendicular to A1).

The instrument box 252 is positioned on the second bracket 276b as shown in FIG. 1. Referring again to FIG. 1A, the instrument box includes a housing 253a removably attached to the second bracket 276b, so that the instrument box may be detached after surgery for disposal or sterilization and reuse. A passage 275 for the surgical instrument 100 extends through the housing as shown. As shown in FIG. 16, in the first embodiment, an opening 253b in the housing 253a is slidable over the proximal portion of the second bracket 276b. A spring latch 255 (FIG. 1A) between the instrument box 252 and bracket 276b engages the two components once the instrument box 252 has been advanced to the proper position.

The instrument box 252 is configured to receive the surgical instrument 100 and to allow the instrument shaft to slide relative to the instrument box 252 during z-axis positioning of the instrument. The arrangement of the first and second brackets 276a, 276b with the instrument box 252 (and therefore the instrument 100) renders the interface 250 moveable about the axes A1, A2 when the user moves the instrument handle. Up-down movement of the instrument handle results in pitch movement of bracket 276b about axis A2, and side-side movement of the instrument handle results of yaw movement of bracket 276a about axis A1, with combined up-down and side-side movement resulting in combined pitch and yaw motion.

Encoders within the command interface 250 generate signals in response to movement about the axes A1, A2. In particular, a first encoder is positioned such that it will generate signals corresponding to yaw movement of first bracket 276a (about axis A1). A second encoder is positioned to generate such signals corresponding to pitch movement of second bracket 276b (about axis A2). Types of suitable encoders include optical or magnetic incremental rotary encoders that generate signals corresponding to the speed and the incremental amount of angular movement are suitable for this purpose. Signals generated by these encoders are received by electronics housed within the base unit 218 and used to control and drive the steering motors 236a, b (FIG. 7B).

The instrument box houses components that cause several types of user input signals to be generated by the system in response to user action, including: (a) signals representing the amount by which the user axially rotates the instrument handle or an associated roll knob; (b) signals indicating proper placement of an instrument 100 into engagement with the system at the instrument box; (c) signals from a user-operable engage/disengage button that lets a user selectively engage or disengage operation of the command interface 250 from activation of the motors; and (d) signals generated in response to z-axis movement of the instrument to indicate the z-axis position of the instrument 100.

Figure 17A:
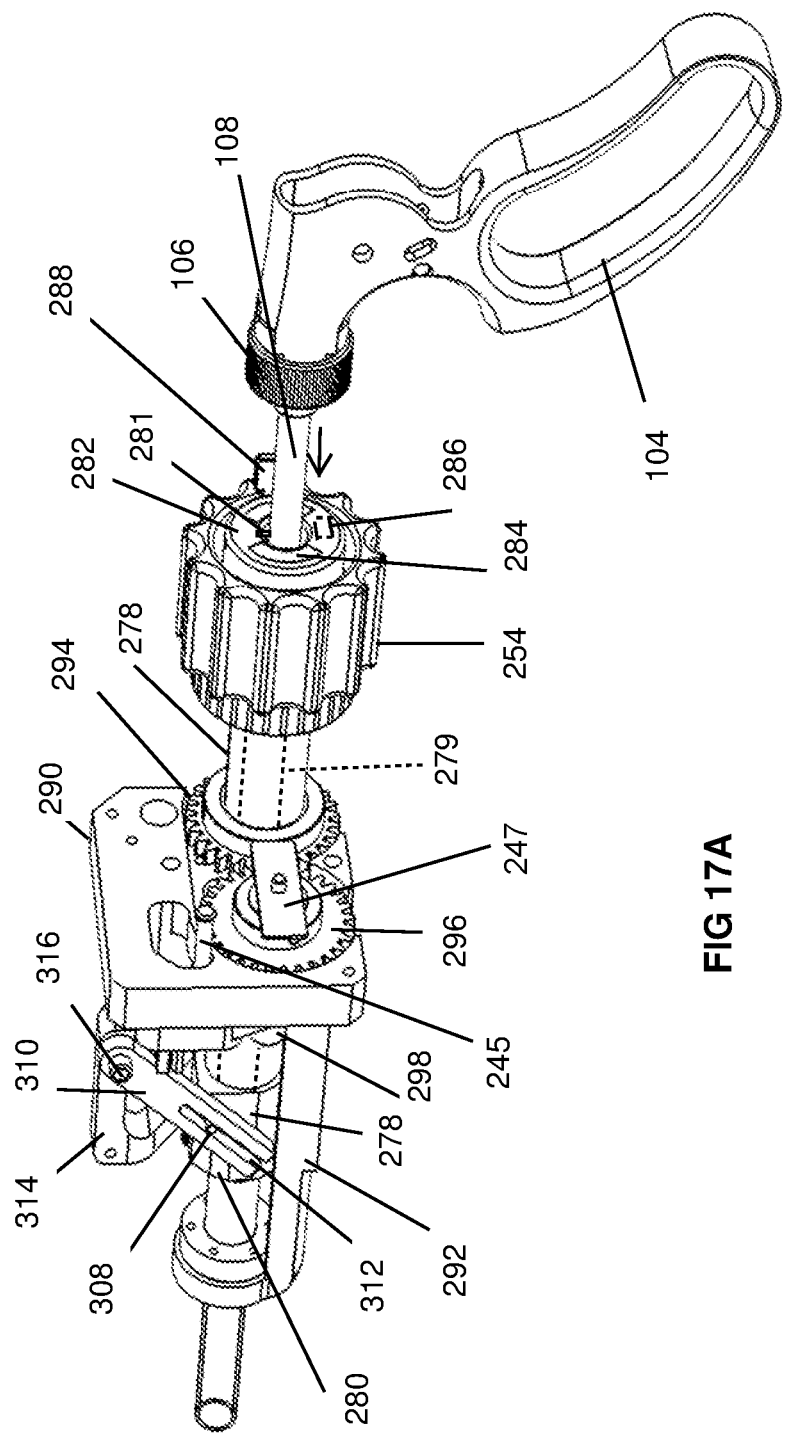
FIG. 17A is a proximal perspective view of the instrument box with the housing removed and with an instrument handle withdrawn from the operative position. The distal shaft of the instrument is not shown.

Referring to FIG. 17A, the instrument box 252 includes an elongate tube 278 having a knob 254 on its proximal end. A lubricious inner tube 279 extends through the elongate tube 278 and has a proximal block 282 surrounded by the knob 254. The block 282 supports one or more exposed metallic elements, such as the proximally-facing metallic elements 284. A magnetic sensor 286 is within the block 282. An opening in the block 282 is positioned to receive the shaft of an instrument 100 so that instrument shaft can pass tube 278. A spring loaded pin 281 extends into the opening in the block 282.

In FIG. 17A, the handle of instrument 100 is shown only partially advanced towards the knob 254 to allow certain features to be visible. A collar 106 is located on a proximal portion 108 of the instrument's shaft. The distal side of the collar 106 is most easily seen in FIG. 11B. It includes a distal part having a notch 109. A magnet 110 in the collar 106 faces distally. These features are located such that when a user advances the instrument 100 through the opening in the block 282 with the notch 109 facing the pin 281, the notch 109 captures the pin 281 to rotationally engage the instrument handle to the block 282. The magnet 110 magnetically adheres to the metallic elements 284 when brought into proximity to them, thus retaining the instrument in position against the block 282.

The sensor 286, which may be a Hall sensor, is positioned so that it will generate an instrument presence signal when the magnet 110 is positioned at the metallic elements 284. This signal alerts the system that an instrument is properly positioned at the command interface 250 and the system is therefore ready to control the steerable fingers and the instrument roll position when the user is ready to do so.

The system may therefore be configured such that the motors used to steer a given finger will not be activated in the absence of an instrument presence signal from the sensor 286, unless the user otherwise overrides this feature. This feature prevents inadvertent movement of a finger when there is no instrument extending through it.

A user actuated switch is positioned to generate a signal indicating whether the user wishes to place the system in an "engaged" state. The switch may be located near the users hand for easy access, such as on the instrument box 252, the instrument, or elsewhere on the system 2. Alternatively, the switch may be a foot pedal or voice activated circuit.

In the first embodiment, the switch is actuated using a button 288 positioned adjacent to the knob 254 and supported by a button assembly (not shown). A magnet (not shown) is carried by the button assembly. When the engage button 288 is pressed, the button assembly moves the magnet into or out of alignment with a Hall sensor, causing the Hall sensor to generate a signal that the button has been pressed. When pressure on the button 288 is released, a spring (not shown) returns the button to its original position. Feedback is provided to the user when the system is moved in and out of the engaged state. For example, an LED 245 on the instrument box can turn on, or change color, when that part of the system is engaged and turn off when it is disengaged. An auditory tone might additionally be sounded when the system is moved between the engaged and not-engaged state. An electrical connector 99 (FIG. 17B) in connected between the instrument box and the bracket 276b to apply a voltage to the LED.

When the engage button has been pressed, the system moves from a "not engaged" state to an "engaged" state with respect to the instrument on that side of the system. When in the engaged state (assuming instrument presence has been detected as discussed above), the system will activate the motors in response to detected movement at the command interface 250. Pressing that same engage button 288 again will generate another signal used by the system to move the system to a "not engaged" state with respect to the instrument on that side of the system. When the system is in the "not engaged" state, the steering and roll motors will not be activated and the orientation of the fingers 214 and the roll drive tube 248 remain fixed. The instrument presence sensor 286 and the user actuated engage button 288 are therefore useful safety and convenience features designed to prevent activation of the steering and roll motors 236a,b, 238 even in the presence of detected movement at the command interface 250. This is beneficial in a variety of circumstances, such as when the user wishes to remove his/her hand from the instrument handle without causing inadvertent movement of the fingers within the body as the command interface 250 shifts position or is inadvertently bumped. The user might also wish to disengage the system in order to maintain the orientation of a finger 214 within the body cavity while s/he re-positions the command interface to a more ergonomic position, or while s/he replaces the instrument extending through that finger with another instrument s/he wants to deliver to the same location within the body.

If the user elects to change the position of the button 288 relative to the instrument handle 104, s/he may do so by rotating instrument collar 106 relative to rotation knob 254.

A cord (not shown) extending between the block 282, knob 254 or adjacent structures may be used to carry signals from the instrument presence sensor 286 and the sensor associated with the user actuated button 288 to circuitry in the base or command interface 250.

Roll Input

The instrument box 252 gives the user two ways in which to trigger motorized rolling of the instrument's shaft. The first way is to spin the knob 254; the second way is to rotate the instrument handle 104. In the first embodiment, the rotation knob 254 is positioned near the instrument handle 104, allowing the user to find the knob in a position similar to the position of a rotation knob on a standard hand instrument.

Figure 17B:
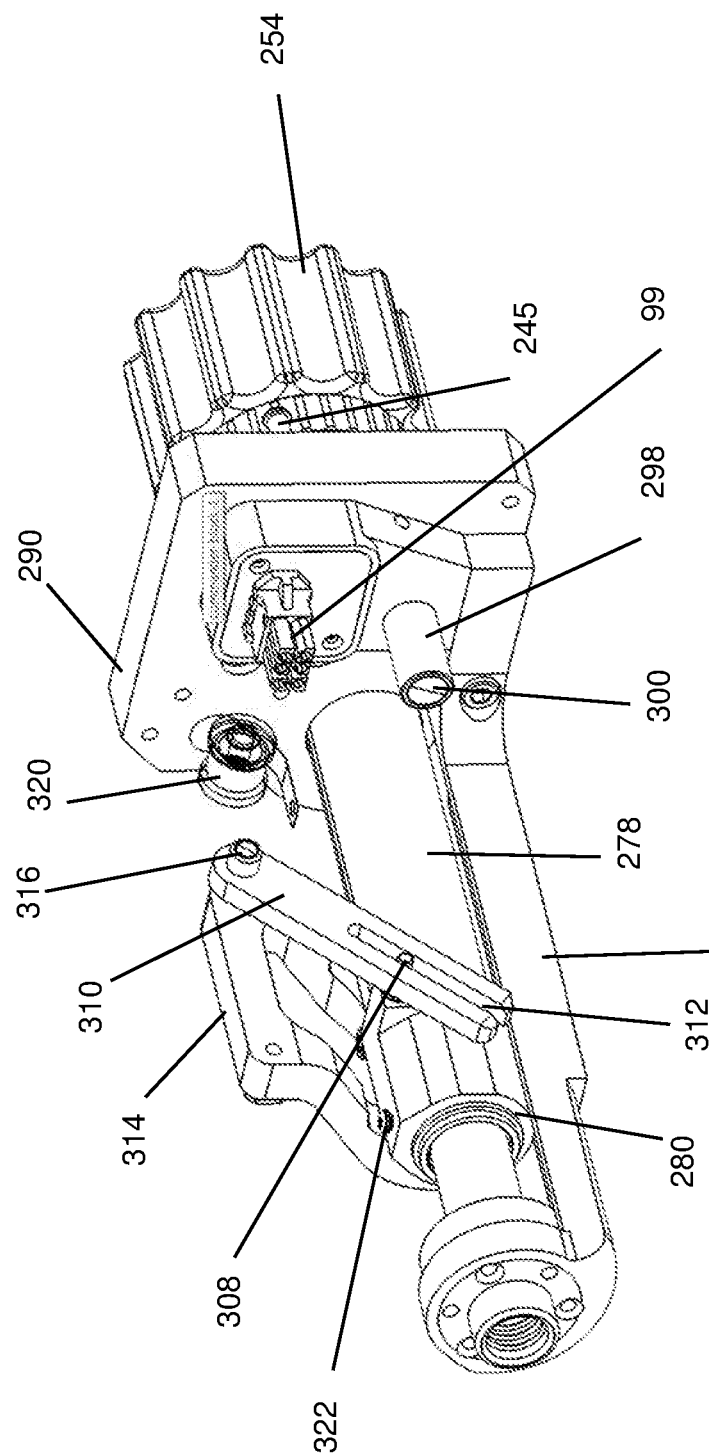
FIG. 17B is a distal perspective view of the instrument box with the housing removed.

Supports 290, 292 are mounted in fixed positions within the instrument box 252. A first gear 294 is rotationally engaged with the exterior surface of the tube 278, and a second gear 296 is adjacent to and engaged with first gear 294. Knob 254, tube 278, and thus gear 294 are axially rotatable relative to instrument box 252, and their rotation produces corresponding rotation of the second gear 296. Rotation of the second gear 296 produces rotation of a magnet positioned such that rotational position of the magnet is sensed by an encoder in the command interface 250. There may be a sterile drape present between the magnet and encoder. Referring to FIG. 17B, the magnet is a disk magnet 300 supported on a post 298. The post 298 extends distally from the second gear 296 and rotates when the gear rotates. The magnet 300 includes a distally-facing surface having diametrically positioned north and south poles.

When the instrument box 252 is mounted on the bracket 276*b*, the post 298 extends into a corresponding opening 302 (FIG. 16) in the bracket 276*b*. An encoder chip 304 is positioned within the opening 302 so as to sense the rotational position of the magnet 300 on the post 298 (which indicates the rotational position of the knob 254). Signals generated by the encoder chip 304 are used to generate drive signals for the roll motor in response to rotation of the knob 254. Roll input is similarly generated through rolling of the instrument's handle. Because the instrument's collar 106 is rotationally coupled to the tube 278 (via block 282), rotating the instrument handle rotates the tube 278, and results in the generation of a signal at the encoder chip 204 as described above.

In an alternative embodiment, a rotatable knob on the instrument's handle may be rotatable to generate the roll input signals in a similar manner.

Because there is friction at the instruments roll joint 260 (FIG. 11A) between the distal portion 102 of the instrument shaft and the proximal portion 108 of the instrument shaft, rolling of the distal portion can result in a slight roll of the proximal portion 108 which can generate roll input by the roll encoder chip 204. Referring to FIG. 17A, the instrument box 252 is designed to apply friction against rotational movement of the gear 296 using an element positioned between the instrument box 252 housing (or another fixed support within the instrument box) and the gear 296 or post 298. A friction plate 247 has a first face in contact with the proximal end of the gear 296 or post 298, and a second face in contact with the interior of the instrument box 252 (not shown in FIG. 17A). The friction plate 247 imparts frictional resistance against rotation of the gear 296. The amount of friction is selected such that it is more than the friction present between the distal shaft 102 and the proximal shaft 108 at the instrument roll joint 260. Rotation of the proximal portion of the instrument shaft 108 resulting from friction at the roll joint 260 is thereby prevented from becoming input to the roll encoder chip 204, thus preventing forward feedback.

Z-Axis Movement

Z-axis movement of the instrument to move the instrument tip proximally or distally within the body cavity is manually performed by pushing/pulling the instrument handle 104. The instrument box 250 is configured so that the knob 254 and instrument handle 104 can be used to generate instrument roll input regardless of the z-axis position of the instrument handle relative to the instrument box 252. When the instrument's collar 106 is coupled with the block 282, z-axis movement of the instrument (i.e. advancement and retraction of the instrument between distal and proximal positions) causes the knob 254 and tube 278 to likewise move along the z-axis—keeping the instrument and the roll input features engaged throughout z-axis travel. A constant force spring 320 (FIG. 17B) is connected between a collar 280 on a distal portion of the tube 278 and the support 290. When the instrument is advanced in a distal direction, the tube 278 pushes the collar 280 distally, against the force of the spring 320. When the user removes the instrument handle 104 from the instrument box 252, the spring 320 retracts the tube 278 and thus the collar 280 returns to the proximal position. When an instrument is present the spring 320 force would be less than the frictional force required to move the instrument, and the instrument would maintain position with no user input.

The instrument box may include a lock to prevent the tube 278 from advancing distally during insertion of an instrument into the tube 278. The lock may be a mechanical latch manually releasable by the user or electronically released in response to a signal produced by the instrument presence sensor.

The features of the instrument box allowing the z-axis position of the instrument to be determined will next be described with continued reference to FIG. 17B. A pin 308 extends laterally from the collar 280. A lever arm 310 has a first end having a slot 312 slidable over the pin 308. A second end of the lever arm 310 is pivotably coupled to a stationary lever arm mount 314 mounted within the instrument box. A magnet 316 is positioned at the pivot axis of the lever arm 310, and rotates as the lever arm 310 pivots. The magnet 316 includes a distally-facing surface having diametrically positioned north and south poles.

Referring to FIG. 16, when the instrument box 252 is mounted on the bracket 276*b*, the magnet 316 (FIG. 17A) is positioned in alignment with an encoder chip 318 mounted in the bracket 276*b*. The encoder chip 318 generates signals representing the rotational position of the magnet 316 and thus lever arm 310, from which the axial position of the tube 278 and thus the instrument 100 can be derived by the system.

A scaling factor is the amount by movement of the instrument or finger is scaled upwardly or downwardly relative to the user's movement of the instrument handle. The system 2 uses the determined z-axis position of the instrument to dynamically adjust the scaling factors used in control of the steering motors. For example, smaller scaling factors might be used for steering when the instrument is fully extended from the finger than would be used when the instrument tip is closer to the tip of the finger to give consistent steering relative to the user input regardless of the instrument's z-axis position.

The first and second brackets 276*a*, *b* of the command interface 250 may be covered by sterile drape for use, while the instrument box 252 remains external to the drape.

Electromechanical Block Diagram

FIG. 18A shows an electromechanical block diagram of the system 2, as slightly modified for an embodiment in which a roll input wheel is positioned on the instrument shaft rather than on the instrument box as discussed above. Certain other features, including the deployment sensor, are not shown, and in the FIG. 18A embodiment the roll driver is included as part of the base unit (labeled "Drive Assembly") rather than as a separate component.

Use

To use the system 2, the base unit 218 and the first and second portions 276*a*, 276*b* of the command interface 250 are covered by a sterile drape. The housing 210 of the finger drive assembly 200 and roll driver 216 are mounted to the base unit to engage the motor driven members 228*a*, 228*b*, 244 of the base unit 218 with the driven members 226*a*, *b*, 234. The system monitors engagement between the shafts 228*a*, 228*b*, 244 of the base unit with the shafts 226*a*,*b*, 234 of the finger and roll drivers, and shafts 228*a*, 228*b*, 244 found to not have not engaged with their counterparts may be rotated slightly through motor activation as described in "Motion Transfer" section above.

The instrument box 252 is mounted to the second portion 276*b* of the command interface 250. Spring latches 255 engage to secure the housing 210 and roll driver 216 to the base unit 218 when the components are properly aligned. Similar spring latches are engaged to secure the instrument box 252 to the portion 276b of the command interface.

Sterile tubular connectors 268 are coupled between the roll driver 216 and the port 222 on the housing 210, and similar connectors may be positioned between instrument box 252 and the roll driver 216. Once the system 2 is assembled, the distal end of the finger drive assembly 200 is positioned within the body cavity of the patient. Alternately, the finger drive assembly may also be positioned inside the patient and then assembled to system 2. For easy insertion into the body cavity, the deployment mechanism is used to position the fingers 214 in a streamlined side-by-side configuration using the links 12. The fingers 214 and a portion of the insertion tube 212 are the passed through the incision into the body cavity. The distal tip of a medical instrument (e.g. forceps, graspers or other flexible shaft hand instruments) is inserted through the instrument box 252 and advanced distally. Advancing the instrument causes the tip to exit the instrument box 252, pass through the roll driver 216, then into port 222 on the proximal end of the finger drive assembly's housing 210, and through the corresponding finger 214 until the distal end of the instrument extends from the distal end of the finger 214.

When an instrument is fully inserted through the command interface 250, instrument presence signals are generated at sensor 286 (FIG. 17A).

Additional instruments such as scopes, graspers and the like are passed through the insertion cannula via ports 220 for use simultaneously with the instruments deployed through the fingers.

The deployment mechanism is used to adjust the lateral spacing of each finger (and thus the instrument passed through it) relative to the longitudinal axis of the insertion cannula as described with respect to FIGS. 2A through 2C.

Before the user can steer or roll the instrument using the system, s/he presses the engagement button 288 to cause the system to enter into the engaged state.

At least when the system is placed in an engaged state, the system senses the positions of the brackets 276a,b and the roll input magnet 300 to determine the starting position of the instrument's handle 104.

If the system is in an engaged state and the instrument's presence has been detected, the system will respond to steering and roll input at the command interface 250 by engaging the steering and roll motors to steer the finger and roll the instrument. To steer the instrument 100 within the body, the user manipulates that instrument's handle 104. For example, to move the instrument's end effector upwardly, the user will lower the handle; to move the end to the left, the user will move the handle to the right. (Although in alternate arrangements, the system may be configured such that the end effector moves in the same direction as the handle—so that, for example, raising the handle raises the end effector). The encoders in the command interface 250 sense the movement or position of the handle by sensing rotation of the brackets 276a, b relative to axes A1, A2. In response, the system generates control signals to activate motors 236a, b to thereby steer the finger and the instrument that extends through it. To axially roll the instrument, the user axially rolls the instrument handle 104 or the rotation knob 254 relative to the instrument box 252, producing signals at the roll encoder chip 304. In response the roll motor 238 is activated to roll the distal part 102 of the instrument shaft. To position the instrument further into the body cavity, the user pushes the instrument handle 104 distally. This z-axis movement of the instrument is sensed by encoder 318, and the z-axis position of the instrument may be used by the system to dynamically adjust scaling factors for finger steering and/or instrument roll.

Figure 18B:
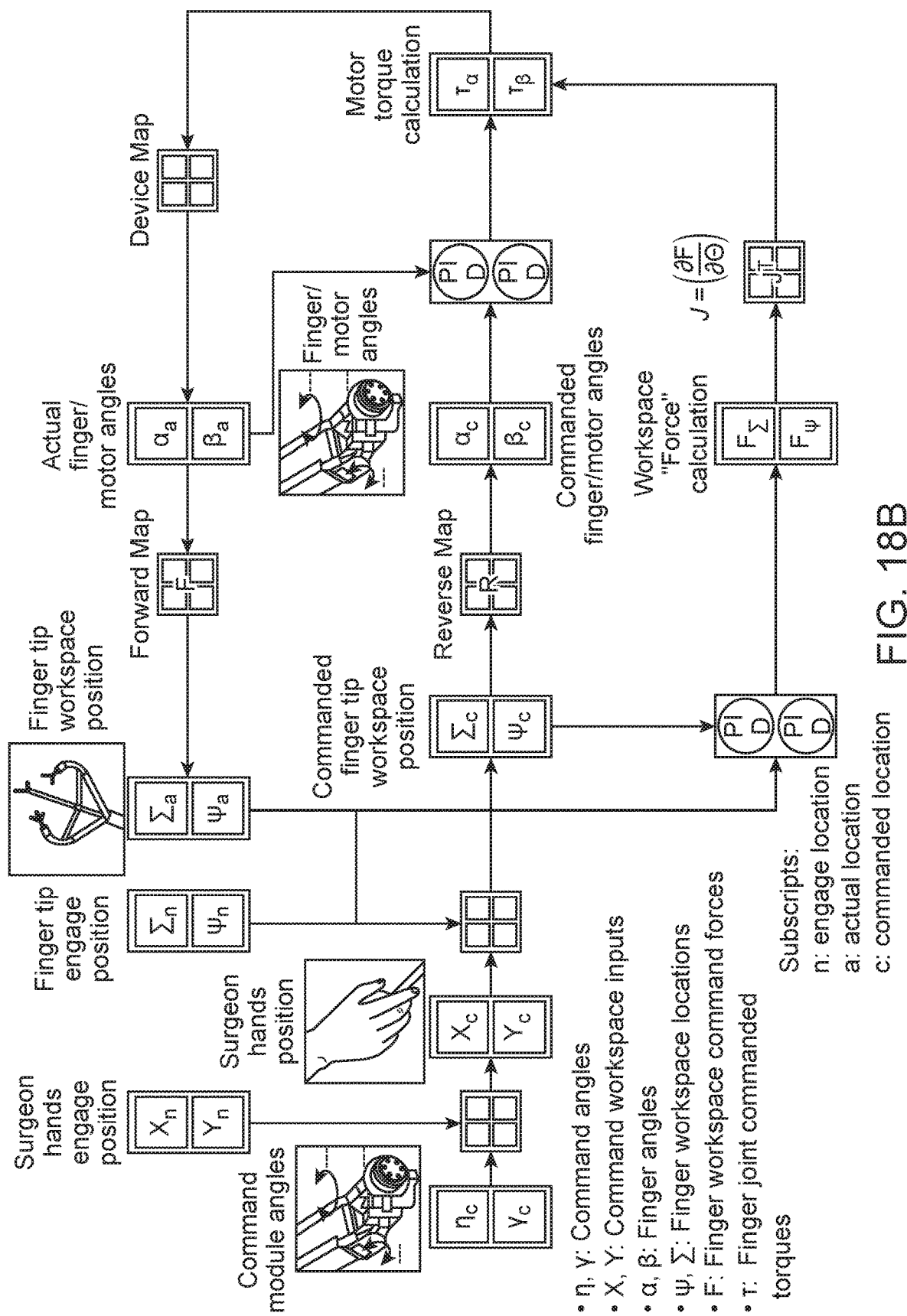
FIG. 18B schematically illustrates an exemplary algorithm for controlling movement of the fingers by the system.

FIG. 18B is a schematic of an exemplary drive control sequence for controlling the steering motors to drive the fingers based on sensed information (e.g. approximations of the positions of the fingers, the positions of the user interface etc), using forward and reverse mapping and PID control.

Actuation of the instrument's end effector, such as the opening/closing of jaws, is carried out in conventional fashion using manual actuators (e.g. levers, knobs, triggers, slides, etc.) on the instrument handle. If desired, an instrument may be withdrawn from the system during the procedure, and replaced with a different instrument, which again may be steered and axially rotated through manipulation of the handle as described.

The first embodiment is but one example of ways in which the mechanized system may be configured. Various modifications may be made to that embodiment without departing from the scope of the invention.

A few such modifications will next be described, but many others are possible and within the scope of the invention.

While the drawings show the two finger drivers in the housing 210 and each roll driver 216 in a separate housing, other embodiments use different layouts. For example, the design may be modified to position the roll drivers 216 in a common housing with the finger drivers. As a second example, the roll drivers 216 might both be mounted in a common housing that is separate from the housing 210 containing the finger drivers. In another embodiment, the roll driver and finger driver associated with the left-instrument may be a common housing, with a separate housing used for both the roll driver and finger driver associated with the right-instrument. Other embodiments might package each of the roll drivers and finger drivers as four separate components.

In other embodiments, the motors are integrated into the assemblies of the corresponding finger drivers and the roll drivers rather than being detachable from them.

Second Embodiment

Figure 19:
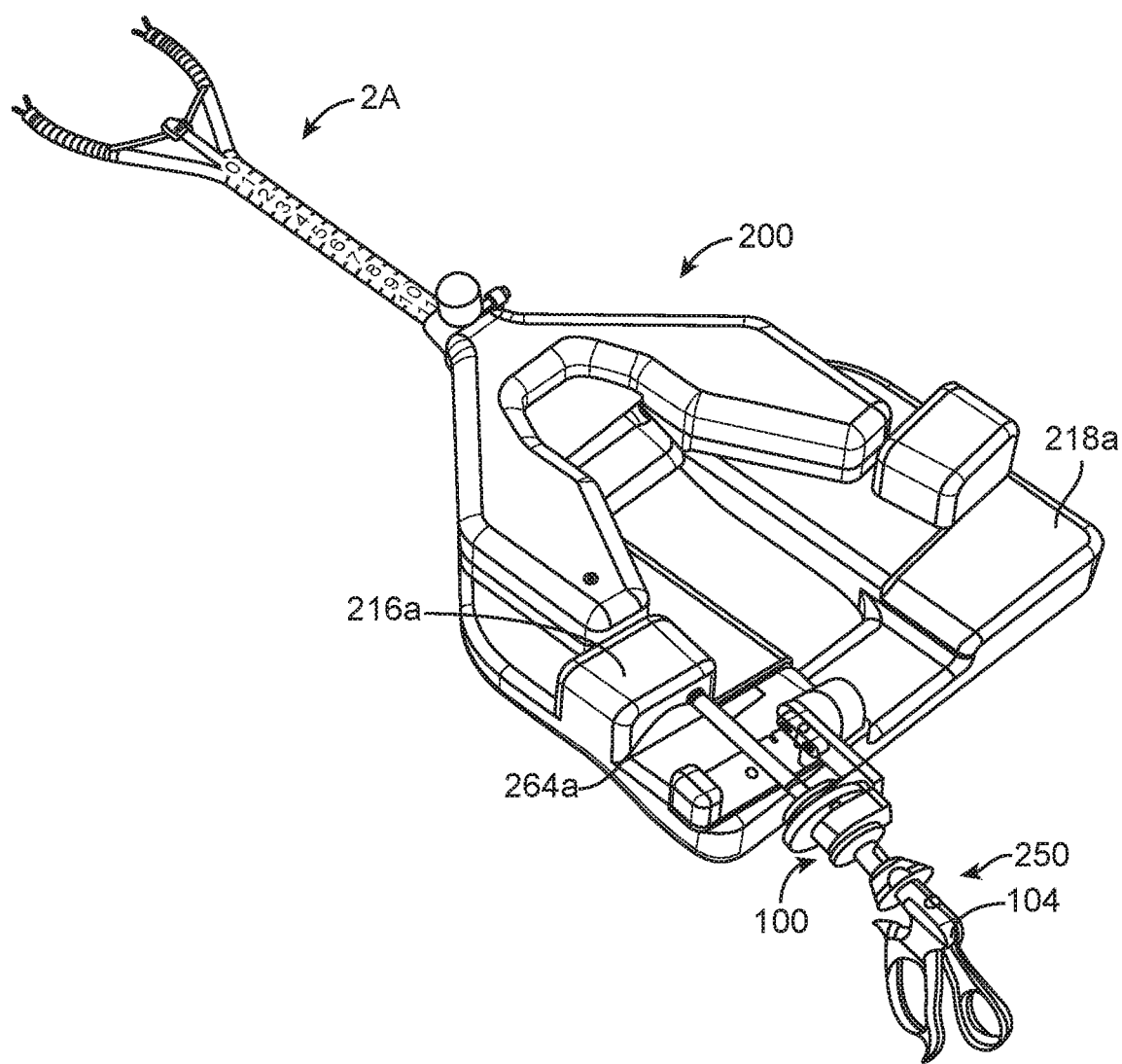
FIG. 19 is a perspective view of a second embodiment.

The system 2A of the second embodiment, shown in FIG. 19, differs from the first embodiment primarily in that the features of the roll driver are incorporated into the base. More particularly, a base 218a includes an elevated portion 216a that houses the roll drive tube 248 (not shown). An instrument passage extends between a proximal opening 264a and a distal opening (not shown) in the elevated portion 216a. The instrument shaft extends through the passage elevated portion 216a between the command interface 250 and the finger drive assembly 200. A sterile tubular insert (not shown) is insertable through the instrument passage in the elevated portion 216a to prevent the instrument 100 from contaminating the passage.

Third Embodiment

Figure 20:
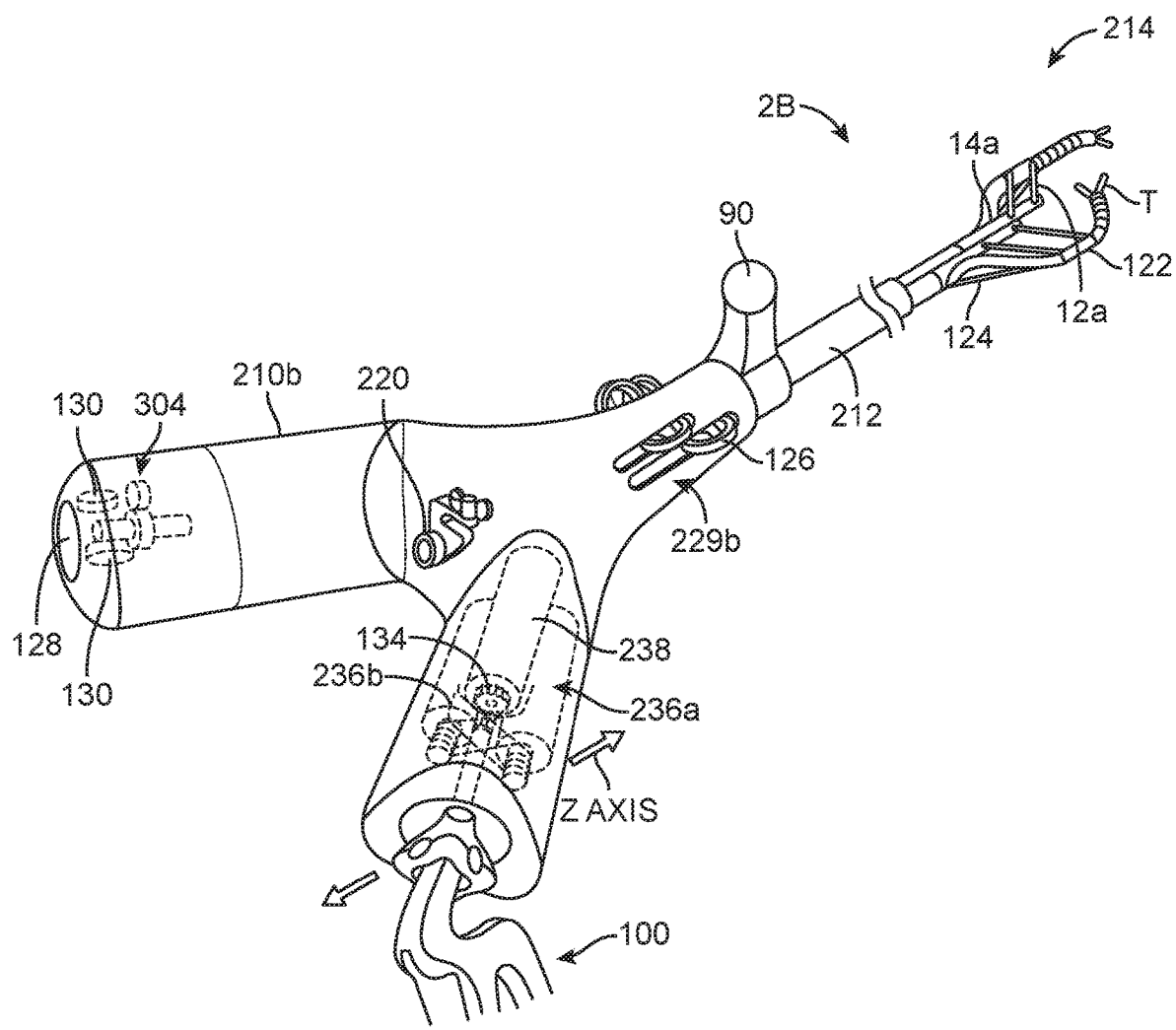
FIG. 20 is a perspective view of a third embodiment.

Referring to FIG. 20, a third embodiment of a surgical access system 2B includes a body 210a and an insertion cannula 212 extending distally from the body 210a. Fingers 214 extend from the insertion cannula 212. The finger 214 may have properties similar to those described elsewhere in this application.

Each finger includes a dedicated deployment mechanism operable to independently reposition the distal portion of the fingers 214 to increase or decrease its lateral separation from the longitudinal axis of the insertion cannula 212. Each deployment mechanism includes a rigid, longitudinally slidable, member 14a and at least one link arm 12a (two are shown for each finger). The rigid member 14a may be constructed of a proximal portion comprising a straight, single-lumen, tube made of stainless steel or rigid polymeric material, and a distal bar extending from the tubular proximal portion. The distal bar may be integral with a portion of the wall of the tubular proximal portion. Each finger 214 extends distally from the lumen of the tubular proximal portion of the rigid member 14a.

The deployment system works similarly to that described for the first embodiment. Each link 12a has a first end pivotally coupled to the rigid member 118 and a second end pivotally coupled to a corresponding finger 214, proximally of its distal end. In the illustrated embodiment, these pivotal connections are formed at collars 122 disposed on the fingers. The rigid member 14a is longitudinally moveable relative to the insertion cannula 212 to pivot the links 120 inwardly and outwardly. In the illustrated configuration, sliding 14a in a distal direction pivots the second ends of the links 120 outwardly to deploy the corresponding finger or to further separate the finger from the longitudinal axis of the insertion cannula 212. Alternate configurations may operate in reverse, so that retraction of the member 14a increases the separation of the fingers.

Each finger may further include a support member or strut 124 having a first end pivotally connected to the collar 122 and a second end pivotally connected to the corresponding one of the members 14a or to the insertion cannula 212. The support struts 124 support the fingers, helping to maintain the longitudinal orientation of the fingers, and preventing them from sagging or buckling during use.

Slide rings 126 are shown for independently sliding each member 14a longitudinally for finger deployment, allowing the user to advance/retract the member 14a by advancing/retracting the ring 126 relative to the body 210a. The ring may include a ratchet feature function as described in the '307 application, which releasably locks the finger in a chosen longitudinal and lateral position by releasably engaging the longitudinal position of the member 14a. FIG. 20 shows that this arrangement allows each finger to be deployed to have a different amount of lateral separation and longitudinal extension.

The tips T of instruments 100 are shown extending from the distal ends of the fingers. The body 210a includes proximal openings 128 for receiving the instruments. To deploy an instrument 100 from a finger 214, the tip of that instrument is inserted through one of the proximal openings 128 and advanced through the body 210a, insertion cannula 212 and finger until its tip T or end effector extends out of the finger. In the FIG. 20 drawing, the handle 104 for the instrument used through the finger on the left is not shown, so as to allow the proximal opening 128 to be seen.

A primary difference between the third and first embodiments is that the features described for inclusion in the first embodiment's finger drivers, roll drivers, command interface (including the instrument box) and base unit are incorporated into the housing 210a.

Sensors 130 are positioned on the body 210a to sense pitch and yaw movement of the instrument handle 104. Motors 236a, b in the body 210a are engaged with cables that extend through the fingers and that are anchored to the fingers (e.g. at 90 degree intervals) to deflect the fingers according to the sensed position of the handle. For example, a first motor 236a may be positioned to drive a first pair of cables corresponding to yaw motion of the finger distal end, and a second motor 236b may be positioned to drive a second pair of cables corresponding to pitch motion of the finger distal end.

Automation may also be provided for driving axial rotation of an instrument disposed through a finger. A handle sensor 304 is positioned to sense axial rotation of the instrument handle 104, and is operatively associated with a roll motor 238 that will produce or aid an axial roll of the instrument or a finger using gear 134.

As with the first embodiment, actuation of the instrument's end effector, such as the opening/closing of jaws, is carried out in conventional fashion using actuators (e.g. levers, knobs, triggers, slides, etc.) on the instrument handle. If desired, an instrument may be withdrawn from the system during the procedure, and replaced with a different instrument, which again may be steered and axially rotated through manipulation of the handle as described.

The system 100 may include a mount 90 engageable with a stabilization arm such as the arm 204 (FIG. 1B) that can be coupled to a cart, the surgical table or to another fixture within the operating room. The stabilization arm may be manually positionable or adjustable using motor driven joints and telescoping members, allowing the height and orientation of the system 2B to be adjusted using a user input such as foot pedals or other input devices.

Fourth Embodiment

Figure 21:
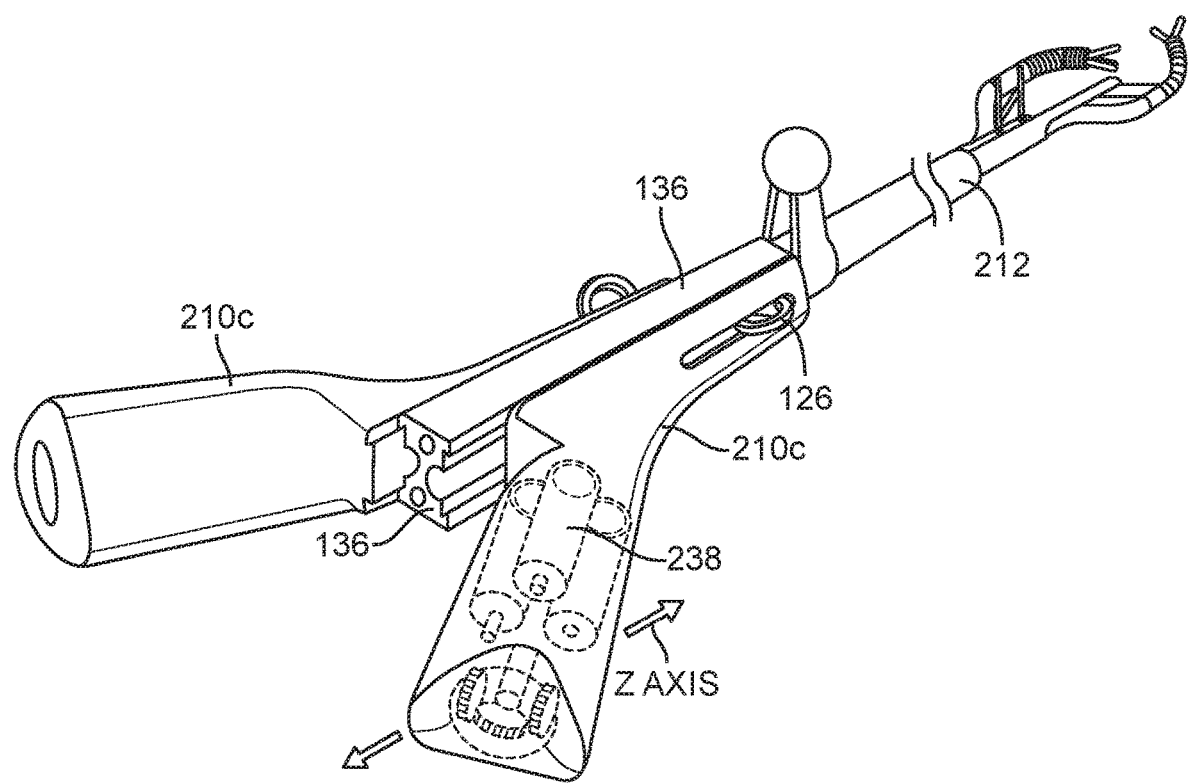
FIG. 21 is a perspective view of a fourth embodiment.

The FIG. 21 embodiment is similar to the FIG. 20 embodiment, but further incorporates a mechanism for Z-axis movement of each finger 214. While use of the slide ring 126 in the FIG. 20 embodiment produces a z-axis change of the corresponding finger position, the FIG. 21 arrangement allows for z-axis movement that is independent of the lateral position of the finger relative to the insertion cannula 212.

In particular, the system has two body sections 210c, each of which is longitudinally slidable along a central track 136. Each body section is coupled to one of the fingers and its corresponding deployment system (member 14a, links 12a, support strut 124, deployment ring 126). In one embodiment, the insertion cannula 212 is coupled to the track 136, and each finger and its drive and deployment systems move longitudinally relative to the cannula in response to manual pushing/pulling by the user. While the primary z-axis adjustment is now carried through on a platform with a linear bearing for each side of the system, the deployment mechanism remains for the adjustment of the tool separation (identified as x-axis in the drawings). Note that each side has an independent deployment system so that the span is independently controlled for each instrument.

Fifth Embodiment

Figure 22:
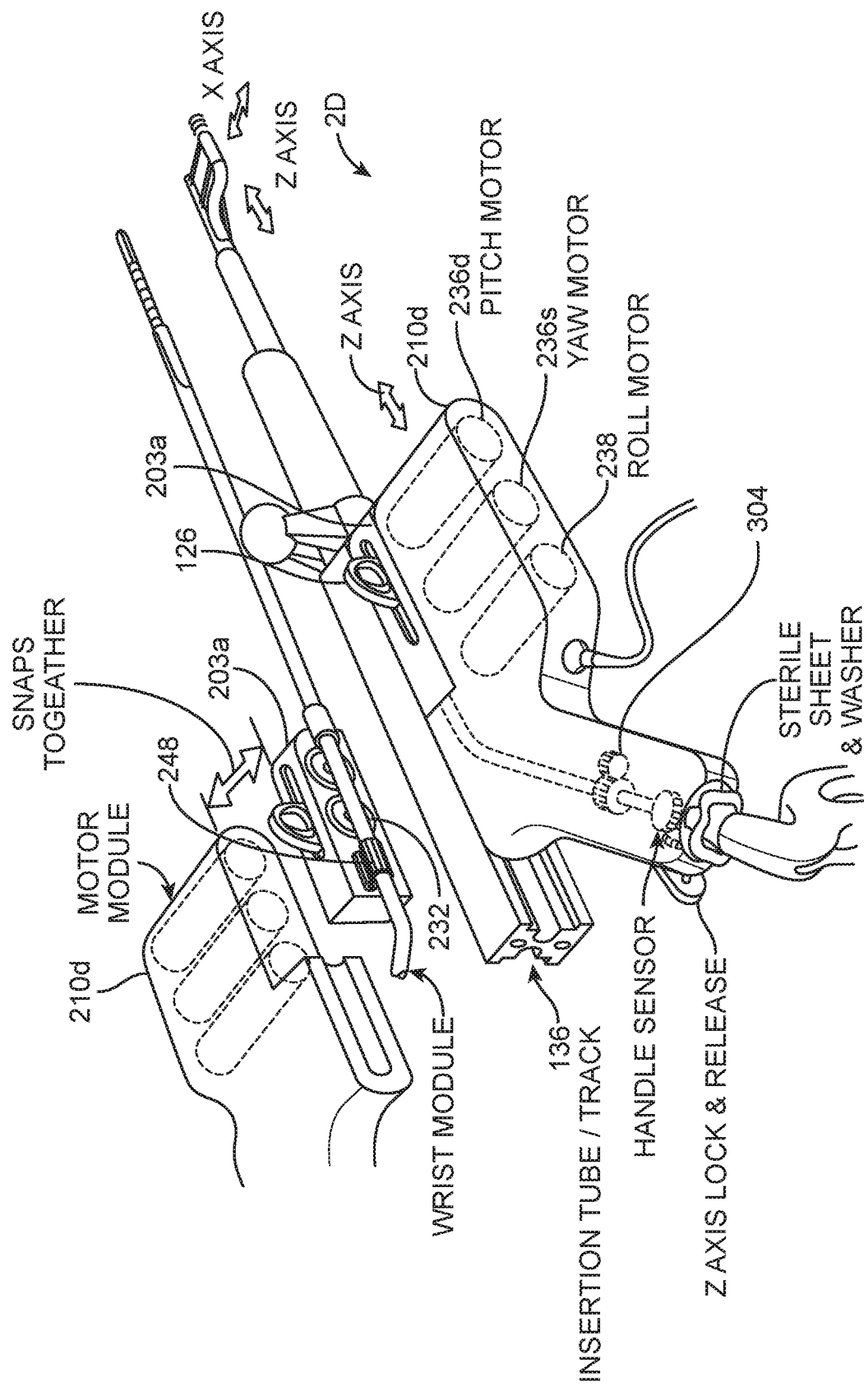
FIG. 22 is a perspective view of a fifth embodiment.

The FIG. 22 embodiment is similar to the FIG. 21 embodiment, but is provided in a more modular format. This embodiment includes independent body sections 210d which house the pitch, yaw and roll motors 236a, b, 230, the sensors 130, 304, and which include the opening 128 for receiving the instrument 100. A pair of finger/roll driver 203a each having pulleys 232, cables (not shown), and a roll drive tube 248 are provided, with each finger/roll driver 203a connected to one of the fingers 214. Each finger/roll driver 203a is releasably engagable with a body section 210d in a manner that allows the motors in the body section 210d module to actuate the pulleys 232 in finger/roll driver 203a so as to tension the cables and roll the finger/roll driver 203a to steer the finger and roll the instrument. Slide rings 126 for finger separation (x-axis) are located on the finger/roll drivers 203a.

Sixth Embodiment

In the FIG. 20-22 embodiments, pitch, roll and yaw are sensed and the finger is electromechanically controlled to position the instrument, however the jaw clamping action or other end effector action of the instrument is mechanically driven by a mechanical actuator on the instrument handle. The FIG. 23 embodiment is largely similar to the FIG. 22 embodiment, but rather than using a hand instrument having a mechanical actuator, it uses an alternate surgical instrument 100a. The instrument 100a engages with a motor 138 in the motor module that is activated to operate the end effector (e.g. jaw) of the tool. In one embodiment, control of the finger and roll drivers is responsive to user manipulation of the instrument 103a to control pitch, roll and yaw as discussed with respect to prior embodiments, but the system is instrument configured to receive signals from an input device (e.g. a switch, foot pedal) to initiate actuation of the end effector via motor 138. In other embodiments, the pitch, roll, yaw and jaw motors may be operable in response to signals received from a separate user input device such as a joystick or other forms of input device(s) rather than manual manipulation of the instrument 103a.

Seventh Embodiment

Figure 23:
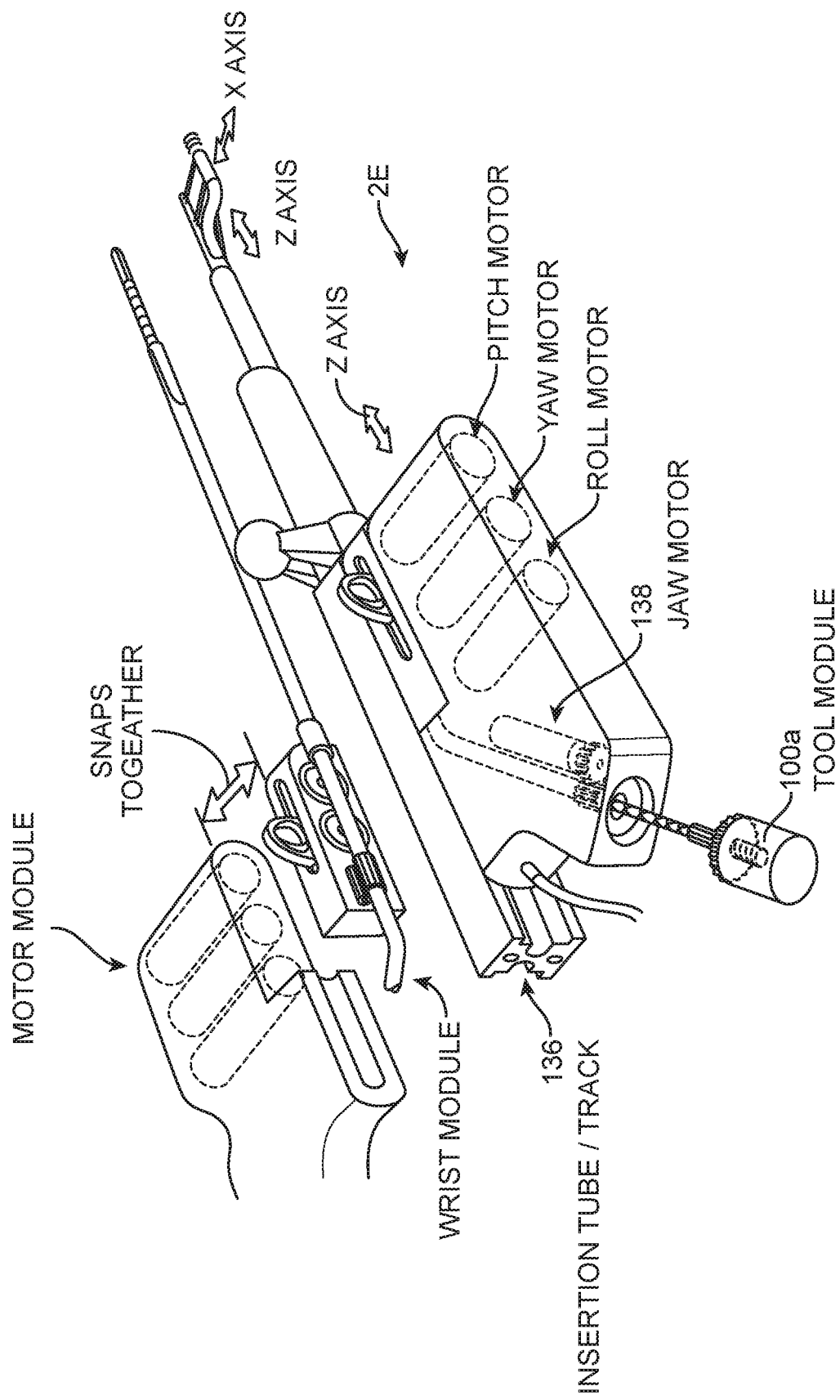
FIG. 23 is a perspective view of a sixth embodiment.
Figure 24:
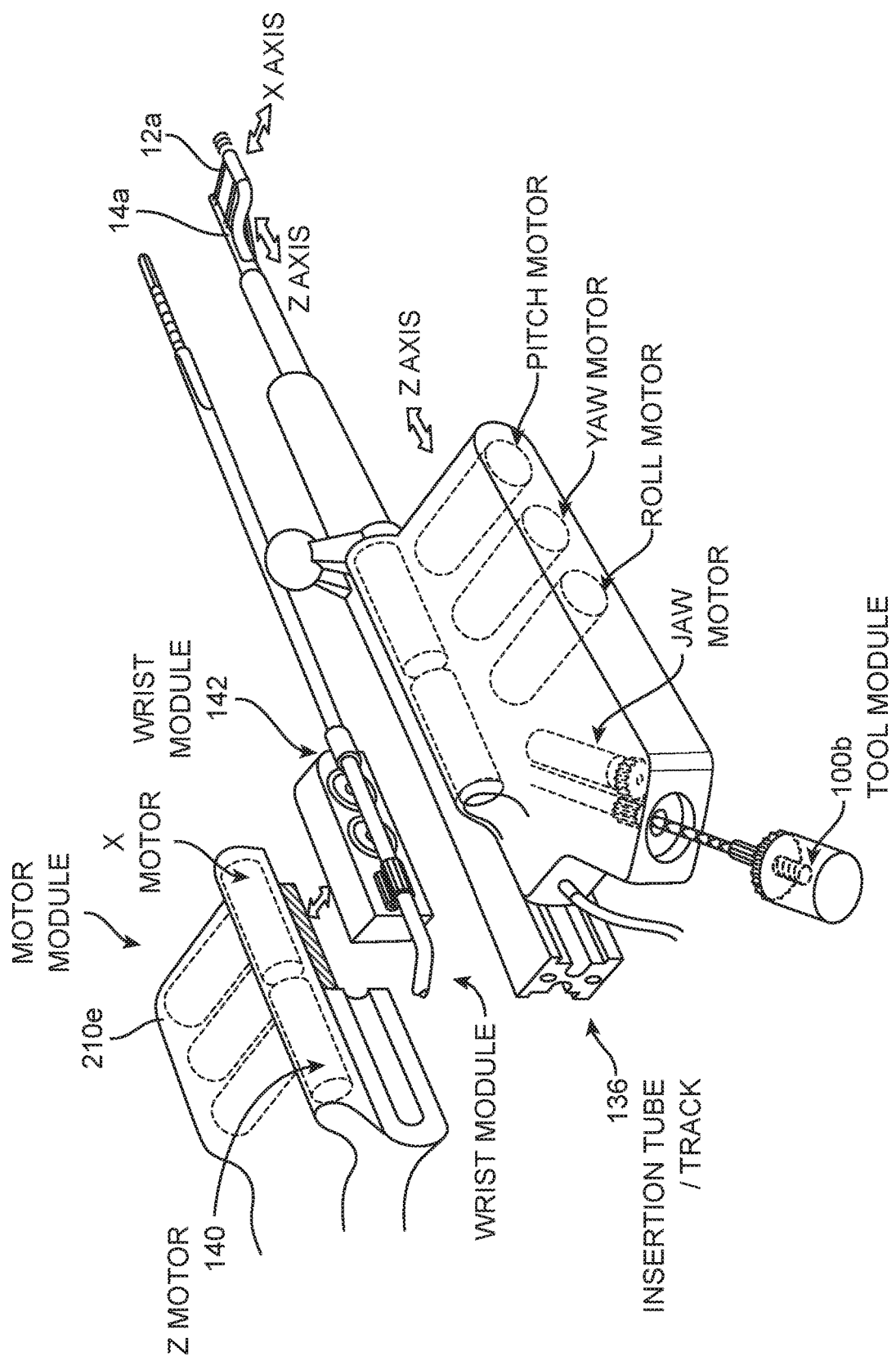
FIG. 24 is a perspective view of a seventh embodiment.

The FIG. 24 embodiment is similar to the FIG. 23 embodiment, but it automates the z-axis movement using a motor 140 that advances/retracts the bodies 210e and the finger/roll driver 203a along the track 136. Moreover, it eliminates the mechanical deployment mechanism and instead automates the x-axis or lateral positioning of the finger using an additional motor 142 in each body 210e. The motor 142 advances/retracts the element 14a to expand the links 12a for deployment and x-axis positioning.

Automating the z- and x-axis movement allows for complex volumetric motions of the instrument beyond what can be achieved using mechanical z- and x-axis movement. Providing a dynamic z-axis increases reach of the instrument while introducing a dynamic x-axis enables complex orientation movements of the instrument tips. Tip movement in the x-direction can in a sense be de-coupled from movement in the z-direction, by automatically adjusting the finger's z-axis position to off-set z-axis changes resulting from pivoting of the links 12a during x-axis adjustments.

Figure 25:
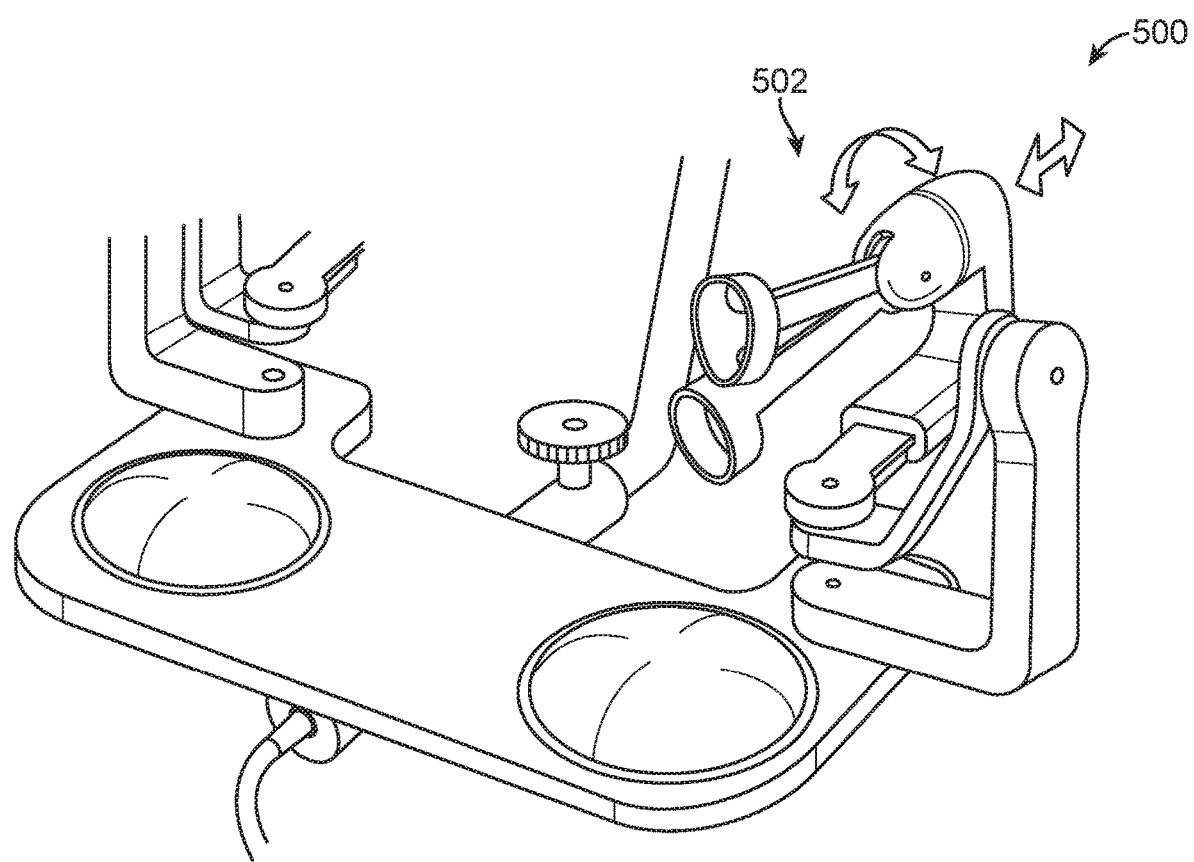
FIG. 25 is a perspective view of a user interface that may be part of the sixth and seventh embodiments.

FIG. 25 shows but one example of a user input device that can be used in systems such as the FIGS. 23 and 24 systems that use input devices that are separate from the instrument handle and shaft. A input device 500 shown in FIG. 25 includes a handle to be manipulated by a user in accordance with the desired position of the surgical instrument. The input device incorporates at least four sensors (associated with multiple pivot joints in a control handle) and an actuator 502 for simulating the grasping load to be achieved at the instrument's end effector. The input device is connected to the body 210d, 210e through digital communication wires and can be located on or near the body 210d, 210e at the patient's bedside, preferably within the sterile field. For example, the input device 500 and the body might be positioned on a common arm (such as arm 204), on different arms supported by a common cart or other fixture (e.g. the operating table or a ceiling mount), or on separate arms on the same or different fixtures. The FIGS. 23 and 24 systems may be provided with various interchangeable tools 100a, each having a different end effector, allowing the user to exchange tool modules as needed during the course of a surgical procedure.

Eighth Embodiment

Figure 26:
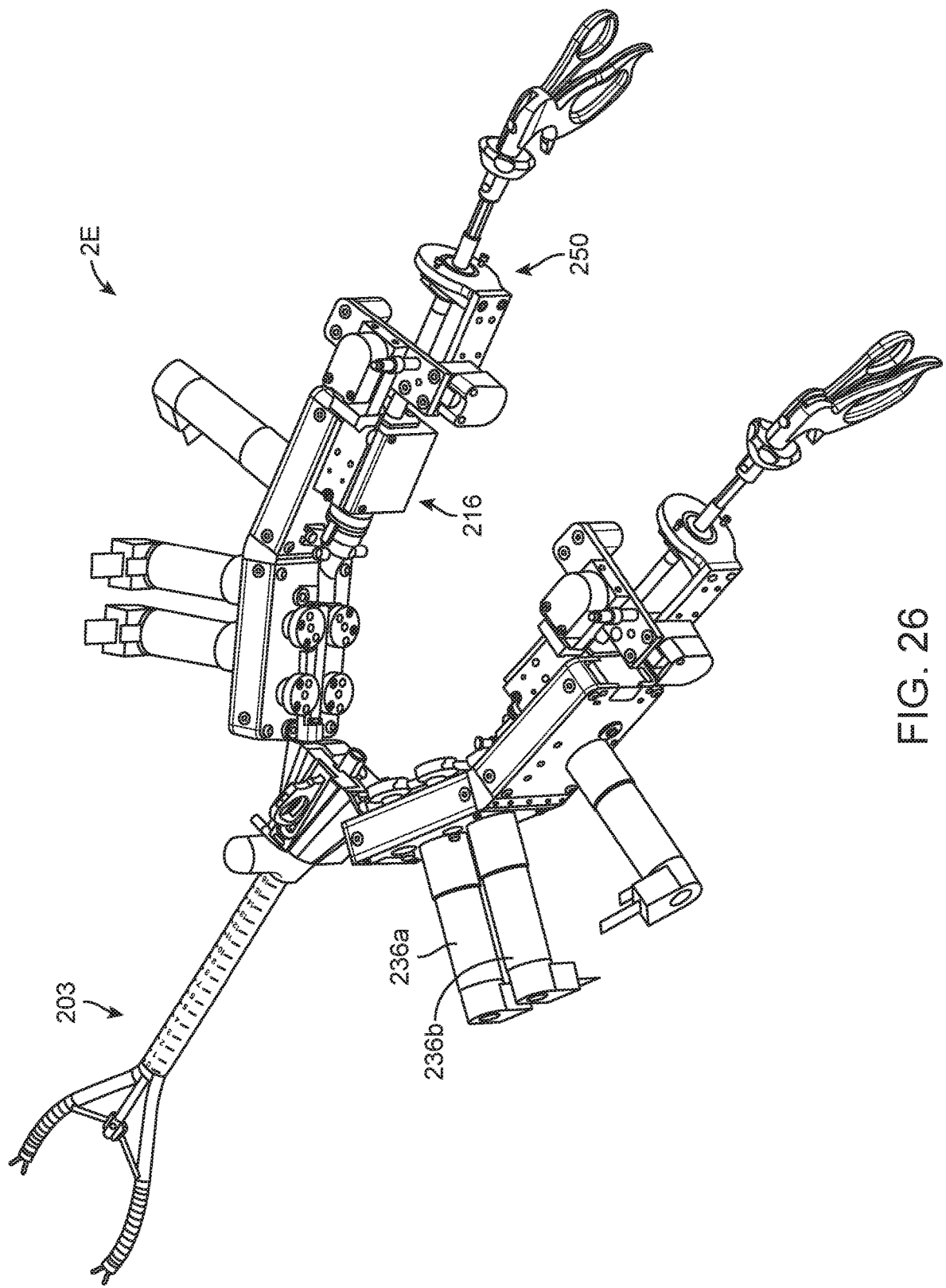
FIG. 26 is a perspective view of an eighth embodiment.

FIG. 26 shows a system 2E that is similar to the first embodiment. However, the finger drive assembly 203, roll drivers 216, command interfaces 250, motor drivers and associated electronics are integrated into a single component. Two steering motors 236a, b are shown on each side of the system 2E, one for each pair of cables. However, each cable may instead have its own dedicated motor.

While certain embodiments have been described above, it should be understood that these embodiments are presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Moreover, features of the various disclosed embodiments may be combined in various ways to produce various additional embodiments.

Any and all patents, patent applications and printed publications referred to above, including for purposes of priority, are incorporated herein by reference.

We claim:

1. A motorized surgical system, comprising:
   at least one support positionable within a sterile field in proximity to a patient positioned on a surgical table;
   an instrument driver carried by the at least one support, the instrument driver having a steerable distal end positionable in a body cavity, the instrument driver comprising a steerable finger having a lumen proportioned to receive a distal portion of a surgical instrument and at least one actuation element extends at least partially through the finger;
   a user input device carried by the at least one support, the user input device configured to generate movement signals in response to manual manipulation of a portion of the user input device by a user; and
   at least one steering motor operably coupled to the instrument driver, the steering motor operable in response to the movement signals to cause tensioning of the actuation element so as to deflect the finger;
   at least one roll driver carried by the support, the roll driver positioned to rotationally couple with a shaft of a surgical instrument that is positioned through the lumen,
   a roll input device carried by the support, the roll input device configured to generate roll signals in response to manual manipulation of the roll input device; and
   a roll motor, the roll motor operably coupled to the roll driver, the roll motor operable to move the roll driver in response to the roll movement signals, wherein:
   the system includes a base mountable on the support, the steering motor is housed within the base and includes a first drive member exposed on the motor housing, and the roll motor includes a second drive exposed on the motor housing;
   the actuation element of the instrument driver is disposed on at least one pulley, and the instrument driver includes a first driven member rotatable to rotate said at least one pulley;

the roll driver includes a tubular member having a lumen proportioned to receive a distal shaft portion of a surgical instrument, and a second driven member rotatable to rotate said tubular member; and the instrument driver and roll driver are removably positionable on the base to rotationally couple the first drive member with the first driven member and to rotationally couple the second drive member with the second driven member.

2. The system of claim 1, wherein:

the roll driver includes a roll driver housing, the tubular member disposed within the roll driver housing and the second driven member exposed at the exterior of the roll driver housing; and the instrument driver includes an instrument driver housing, said at least one pulley disposed within the instrument driver housing and the first driven member exposed at the exterior of the instrument driver housing.

3. The system of claim 2, wherein the roll driver housing comprises the instrument driver housing.

4. The system of claim 2, wherein the roll driver housing and the instrument driver housing are separate housings.

5. The system of claim 1, wherein the instrument driver and the user input device are on a common support.

6. The system of claim 5, wherein said at least one support includes:

a first support positionable within a sterile field in proximity to a patient, the instrument driver carried on said first support; and a second support positionable within the sterile field in proximity to the patient, the user input device carried on said second support.

7. The system of claim 6, wherein the at least one steering motor is carried on the first support.

8. A motorized surgical system, comprising:

at least one support positionable within a sterile field in proximity to a patient positioned on a surgical table;

an instrument driver carried by the at least one support, the instrument driver having a steerable distal end positionable in a body cavity, the instrument driver comprising a steerable finger having a lumen proportioned to receive a distal portion of a surgical instrument and at least one actuation element extends at least partially through the finger, wherein the instrument driver further includes an instrument driver housing;

at least two actuation elements, a first pulley within the instrument driver housing and coupled to one of the actuation elements, the first pulley including a first gear;

a second pulley within the instrument driver housing and coupled to one of the actuation elements, the second pulley including a second gear;

a third gear engaged with the first and second gears; and a driven member exposed on the instrument driver housing a user input device carried by the at least one support, the user input device configured to generate movement signals in response to manual manipulation of a portion of the user input device by a user; and at least one steering motor operably coupled to the instrument driver, the steering motor comprising a motor housing and includes a drive member exposed on the motor housing, the steering motor operable in response to the movement signals to cause tensioning of the actuation element so as to deflect the finger;

at least one roll driver carried by the support, the roll driver positioned to rotationally couple with a shaft of a surgical instrument that is positioned through the lumen, a roll input device carried by the support, the roll input device configured to generate roll signals in response to manual manipulation of the roll input device; and a roll motor, the roll motor operably coupled to the roll driver, the roll motor operable to move the roll driver in response to the roll movement signals wherein the motor housing and the instrument driver housing are positionable to rotationally couple the driven member and the drive member such that activation of the motor rotates the third gear and the pulleys.

9. The system of claim 8, further including a sensor positioned to generate a signal in response to positioning of the instrument driver housing in contact with the motor housing.

10. The system of claim 8, further including a sensor positioned to generate a signal in response to engagement of the first and second engaging members.

11. The system of claim 8, wherein one of the first and second engaging members is a male member and the other of the first and second engaging members is a female member.

12. The system of claim 11, wherein at least one of the first and second engaging members is a depressible member moveable relative to its corresponding housing between an extended position and a partially depressed position, and wherein said depressible member includes a spring positioned such that contacting the first and second engaging members causes the depressible member to move against the spring into the depressed position, and to return to the depressible member to the extended position under action of the spring to cause the first and second engaging members to mate.

13. The system of claim 12, further including a sensor positioned to generate a signal in response to movement of the depressible member from the depressed position to the extended position.

* * * * *